(12) United States Patent
Banerjee et al.

(10) Patent No.: US 10,266,634 B2
(45) Date of Patent: Apr. 23, 2019

(54) CHEMICALLY STABLE HOLLOW SPHERICAL COF AND SYNTHESIS THEREOF

(71) Applicant: Council of Scientific & Industrial Research, New Delhi (IN)

(72) Inventors: Rahul Banerjee, Pune (IN); Sharath Kandambeth, Pune (IN); Digambar Balaji Shinde, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/507,024

(22) PCT Filed: Aug. 28, 2015

(86) PCT No.: PCT/IN2015/050100
§ 371 (c)(1),
(2) Date: Feb. 27, 2017

(87) PCT Pub. No.: WO2016/030913
PCT Pub. Date: Mar. 3, 2016

(65) Prior Publication Data
US 2017/0247493 A1 Aug. 31, 2017

(30) Foreign Application Priority Data

Aug. 29, 2014 (IN) .......................... 2462/DEL/2014

(51) Int. Cl.
| | | |
|---|---|---|
| C08G 12/08 | (2006.01) | |
| C08G 14/06 | (2006.01) | |
| C12N 9/76 | (2006.01) | |
| C12N 11/02 | (2006.01) | |
| C12N 11/04 | (2006.01) | |
| C12N 11/08 | (2006.01) | |

(52) U.S. Cl.
CPC .............. *C08G 12/08* (2013.01); *C08G 14/06* (2013.01); *C12N 9/6427* (2013.01); *C12N 11/02* (2013.01); *C12N 11/04* (2013.01); *C12N 11/08* (2013.01); *C12Y 304/21004* (2013.01)

(58) Field of Classification Search
None
See application file for complete search history.

(56) References Cited

FOREIGN PATENT DOCUMENTS

| | | |
|---|---|---|
| EP | 2832767 | 2/2015 |
| WO | 2014057504 | 4/2014 |
| WO | 2014203283 | 12/2014 |

OTHER PUBLICATIONS

Sun et al. Energy Environ.Sci. (2014) 7: 2071-2100 (Year: 2014).*
International Search report based on co-pending International Application No. PCT/IN2015/050110, dated Apr. 6, 2016, 6 Pages.
Written Opinion based on co-pending International Application No. PCT/IN2015/050100 dated Apr. 6, 2016, 7 Pages.
Kandambeth, Sharath, et al., "Self-Templated Chemically Stable Hollow Pherical Covalent Organic Framework", Nature Communications, Apr. 10, 2015, vol. 6, pp. 1-10.
Das, Gobinda, et al., "Mechanosynthesis of imine, B-Ketoenamine, and Hydrogen-Bonded Imine-Linked Covalent Organic Frameworks Using Liquid-Assisted Grinding", Chemical Communications, Jul. 3, 2014, vol. 50, No. 84, pp. 12615-12618.
Xu Chao, et al., "Synthesis of Microporous Organic Polymers with High CO2-over-N2 Selectively and CO2 Adsorption" Journal of Materials Chemistry A, Jan. 9, 2013, vol. 1, No. 10, pp. 3406-3414.
Chen, Xiong, et al., "Towards Covalent Organic Frameworks with Predesignable and Aligned Open Docking Site", Chemical Communications, Apr. 14, 2014, vol. 50, No. 46, pp. 6161-6163.
Fang, Qianrong, et al., "Designed Synthese of Large-Pore ,Crystalline Polyimide Covalent Organic Frameworks" Nature Communications, Jul. 23, 2014, vol. 5, pp. 1-8.

* cited by examiner

*Primary Examiner* — Susan M Hanley
(74) *Attorney, Agent, or Firm* — McCarter & English, LLP

(57) ABSTRACT

This present invention relates to a chemically stable hollow spherical covalent organic framework having mesoporous walls with high surface area and a process for synthesis thereof. Further the immobilization and adsorption ability of the said COF's is disclosed in the present invention.

12 Claims, 26 Drawing Sheets

CHEMICALLY STABLE HOLLOW SPHERICAL COF AND SYNTHESIS THEREOF

TECHNICAL FIELD OF THE INVENTION

This present invention relates to a chemically stable hollow spherical covalent organic framework COF (DhaTab) having mesoporous walls with high surface area. The present invention further relates to a method for the preparation of chemically stable, macroporous hollow spherical COF by a self-templating method.

BACKGROUND AND PRIOR ART OF THE INVENTION

Research in the linking of organic building units through strong bonds has yielded microcrystalline materials of covalent organic frameworks based entirely on strong covalent linkages between building units. These covalent organic frameworks (COFs) represent an emerging family of crystalline porous materials, with a well-defined and predictable network of molecular building blocks. These materials have potential applications in the field of gas storage, optoelectronics, catalysis and sensing because of their crystalline and periodic structure with high surface area and thermal stability. COFs are usually synthesized as microcrystalline powders and their long range growth is limited in the nano/micro domain due to the internal defects. COF crystallites have been reported to have adopted various shapes such as belts, fibres, sheets, cubes, rectangular prisms etc. However, the mechanisms of the formation and self-assembly of COF crystallites are still poorly understood. The shape of a crystallite is an extremely important factor in molecular absorption and catalysis. In this regard, hollow spherical structures are considered to be an important morphology because of their potential application in catalysis, drug delivery, as molecular sensors and in energy storage. Although active research on the design and synthesis of COFs has been ongoing for almost a decade, there has been only one report of a COF with hollow spherical morphology without much structural (due to poor crystallinity) and mechanistic insight of the hollow sphere formation (Microporous organic network hollow spheres by Kang N et al published in *J Am Chem Soc.* 2013 Dec. 26; 135(51):19115-8). These hollow microporous organic networks (H-MONs) were prepared by a template method using silica spheres. Moreover, the mixed morphology of the sheets and spheres are reported to be found in the reaction medium thus making the isolation of pure hollow spheres extremely difficult and the chemical instability makes this hollow spherical COF inefficient for any practical use.

Chen Long et al have reported a general synthetic strategy for converting the representative typical porous structure of two-dimensional covalent open lattice structures into ordered donor acceptor heterojunctions (*Journal of the American Chemical Society* (2014), 136(28), 9806-09). This donor-acceptor strategy by Chen Long et al explored both skeletons and pores of COFs for charge separation and photo-energy conversion. Inspite of the synthesis of porous COF's having the mechanism of donor acceptor heterojunctions, the synthesized COF's do not suggest the loading or immobilization of COF's with biomolecules, or other medically important compounds.

Self-templated synthetic methods are considered to be the most cost effective synthetic methods for hollow sphere synthesis, since they do not need any sacrificial templates. Template free methods further avoid problems such as inevitable shell collapse and the contamination of pores during the template removal. Although self templating has been the major recipe for the synthesis of metal oxide and metal sulfide based hollow spheres, however, self templating method has been less explored to synthesise organic and polymer based hollow spheres.

The present inventors have in an earlier patent application, PCT International Publication No. WO2014203283 disclosed a covalent organic framework comprising porphyrin linked with a hydroxyl aromatic compound synthesized by a self templating method, however the end product synthesized does not yield hollow COF's to facilitate loading or immobilization of biologically important molecules.

The application of COFs are still mostly limited to the storage of gas molecules, since most of the COFs synthesized are microporous in nature and their pores are not large enough to hold the bigger molecules like drugs or enzymes. Even though few mesoporous boronic acid based COFs have been reported in the literature, however, their chemical instability prevents the usage of these materials for the storage of drugs and enzymes.

Therefore, there remains a need in the art to provide covalent organic frameworks (COFs) that are chemically stable, hollow, spherical having mesoporous walls with high surface area so as to meet a variety of biomedical and industrial applications.

OBJECTS OF THE INVENTION

Thus the objective of the present invention is to provide Covalent organic frameworks (COFs) that are chemically stable, hollow spherical COF(DhaTab) having mesoporous walls with high surface area.

Another objective of the invention is to provide chemically stable, macroporous hollow spherical COF using self-templating method.

Yet another object of the invention is to provide a chemically stable covalent organic framework having ability for loading and immobilization of biomolecules and other medically important molecules.

SUMMARY OF THE INVENTION

In line with the above objectives, the present invention provides chemically stable hollow spherical COF (DhaTab) having mesoporous walls with high surface area prepared by self-templated synthesis. Further, the invention provides mechanism of the hollow sphere formation in detail using different microscopic techniques.

In an aspect, the chemically stable hollow spherical COF (DhaTab), reported in the instant invention is characterized by macroporous hollow spherical core having pore width in the range of 500 nm-2 μm wrapped up by the mesoporous COF shell having width in the range of 20-40 nm. The COF-DhaTab of the instant invention is chemically stable and mesoporous having a preferable pore size of 3.7 nm.

In another aspect, the invention provides chemically stable, hollow spherical COF (DhaTab) having mesoporous walls with high surface area ($1500\ m^2g^{-1}$) for the adsorption and storage of the biomolecules and pharmaceutically important drugs into the COF pores.

Immobilization of enzyme into the mesoporous material is very useful for application like biosensors and biocatalysts because it helps to increase the recyclability of the costly enzyme and also improves the stability of enzymes under extreme conditions.

Abbreviations

COF: Covalent organic frameworks
Dha: 2,5-dihydroxyterephthalaldehyde
Tab: 1,3,5-tris(4-aminophenyl)benzeneCOF-(DhaTab): Covalent organic frameworks comprising 2,5-dihydroxyterephthalaldehyde and 1,3,5-tris(4-aminophenyl)benzene.

DETAILED DESCRIPTION OF THE INVENTION

The invention will now be described in detail in connection with certain preferred and optional embodiments, so that various aspects thereof may be more fully understood and appreciated.

The present invention provides a chemically stable hollow, spherical covalent organic framework (COF) having mesoporous walls with high surface area prepared by self-templated synthesis.

In a preferred embodiment, the present invention provides a chemically stable, hollow, spherical covalent organic framework (COF) comprising 2,5-dihydroxyterephthalaldehyde (Dha) and a compound selected from 1,3,5-tris(4-aminophenyl)benzene (Tab) and $N_1,N_1$-bis(4-aminophenyl)benzene-1,4-diamine (Bad).

Accordingly, the invention provides mechanism of the hollow sphere formation in detail using different microscopic techniques at different time intervals. The present inventors have by elemental analysis and peak measurements indicated that self-assembly induced Ostwald ripening is responsible for the hollow sphere formation.

In an embodiment, the present invention provides a chemically stable, hollow, spherical COF selected from Dha-Tab comprising 2,5-dihydroxyterephthalaldehyde (Dha) and 1,3,5-tris(4-aminophenyl)benzene (Tab) and Dha-Bad 2,5-dihydroxyterephthalaldehyde (Dha) $N^1,N^1$-bis(4-aminophenyl)benzene-1,4-diamine (Bad).

Figure 13:
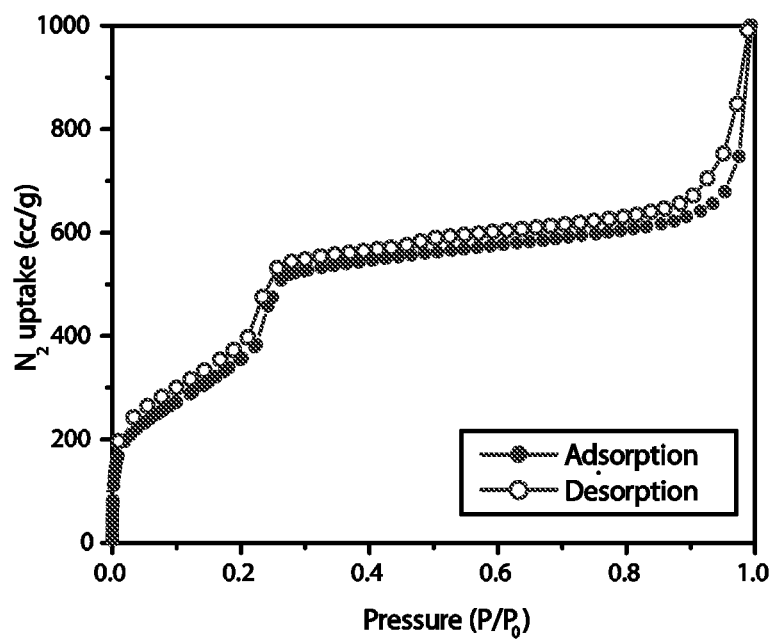
FIG. 13 depicts the $N_2$ adsorption isotherms of DhaTab.
Figure 14:
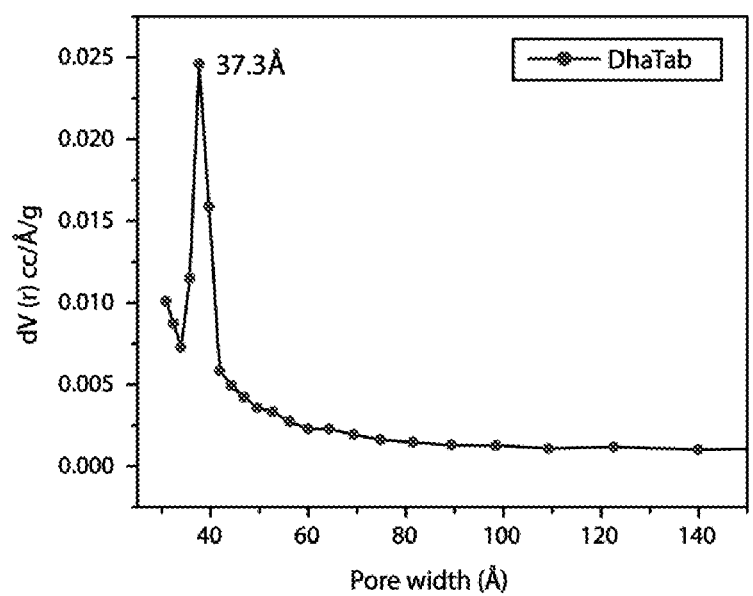
FIG. 14 depicts the Pore size distribution of DhaTab.
Figure 15:
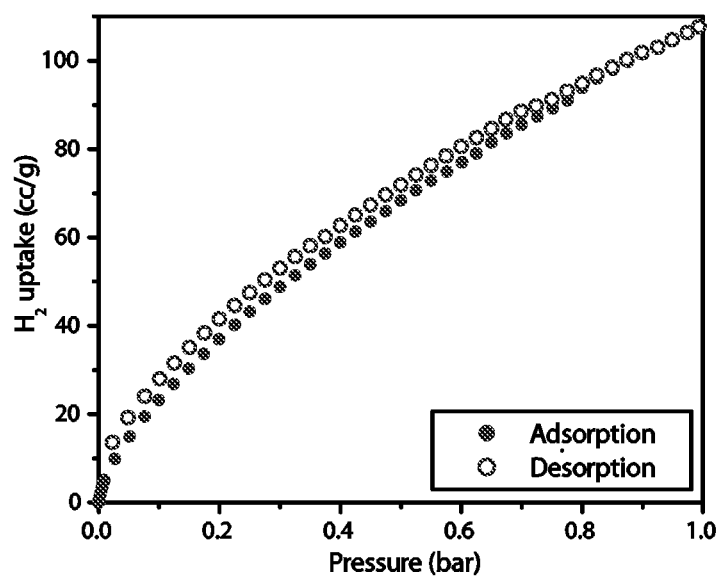
FIG. 15 shows Hydrogen adsorption isotherms of DhaTab at 77 K
Figure 16:
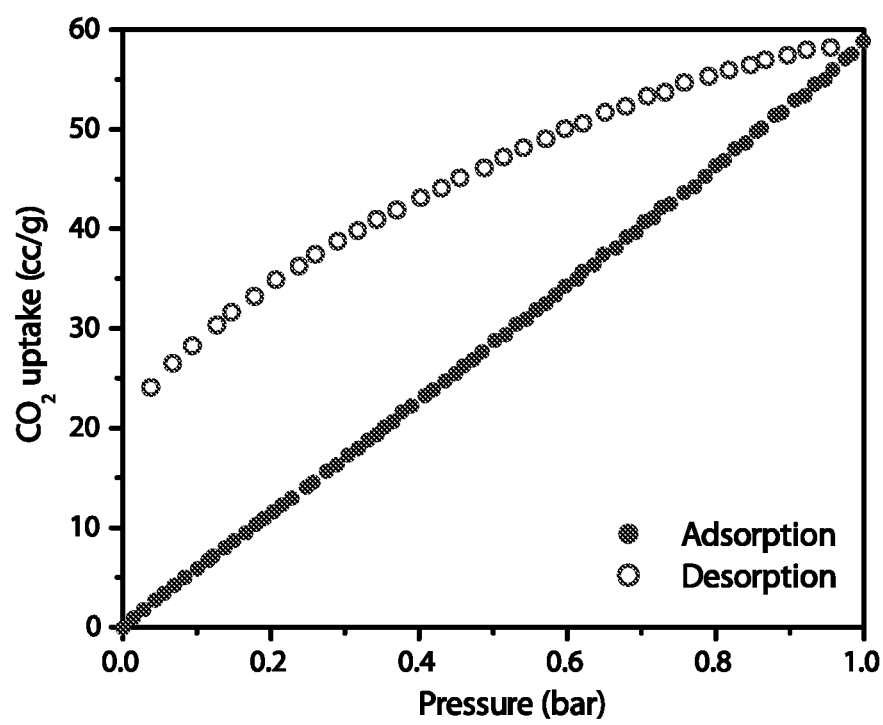
FIG. 16 shows Carbon dioxide adsorption isotherms of DhaTab at 273 K.
Figure 17:
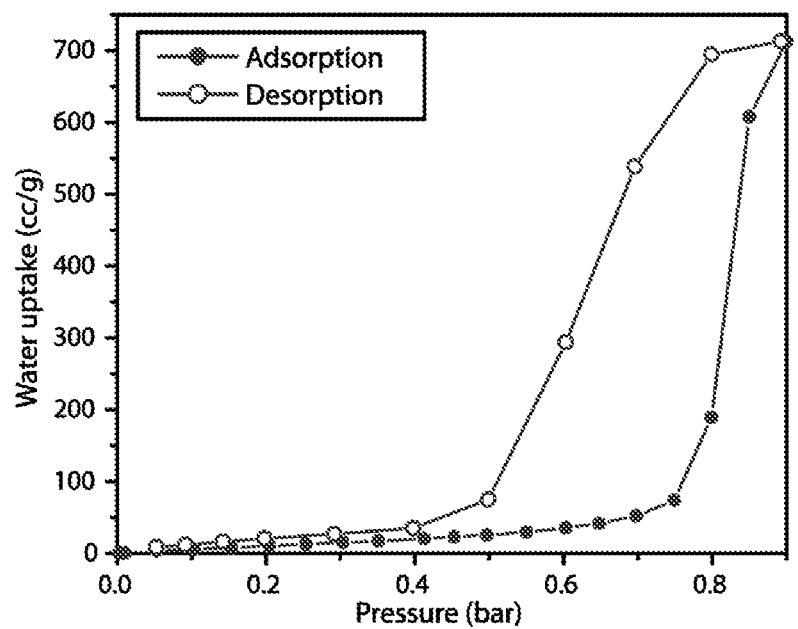
FIG. 17 depicts the water adsorption isotherms of the present DhaTab COF's.
Figure 18:
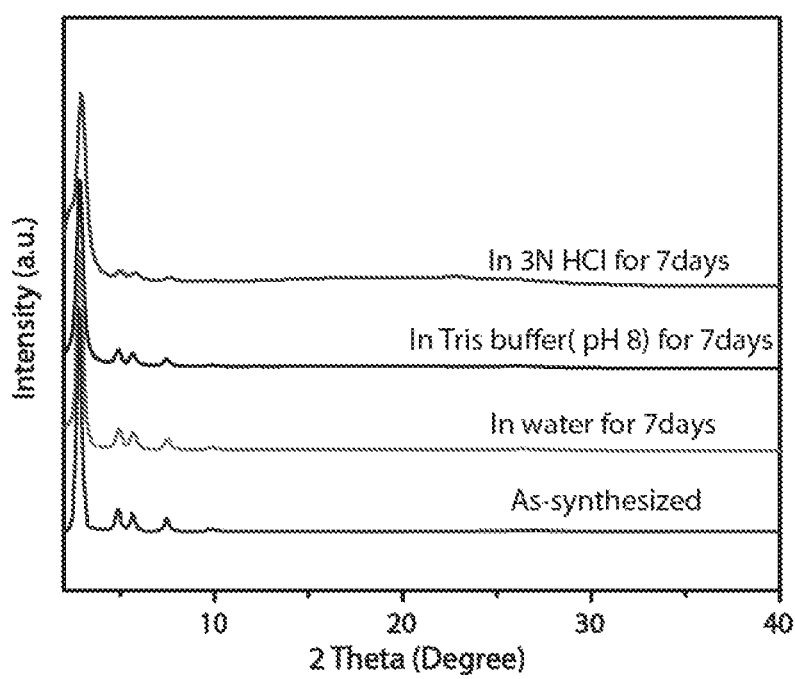
FIG. 18 depicts the morphology of DhaTab after treatment with water, 3N HCl and Tris buffer (pH 8) for 7 days.

The synthesized COF of the present invention is highly crystalline and possesses high surface area in the range of 1200 to 1800 $m^2g^{-1}$. The Dha-Tab COF has a high surface area of 1500 $m^2g^{-1}$. The surface area of COF-DhaTab was calculated to be 1480 $m^2g^{-1}$ (FIGS. 2d and 13). The high surface area of COF-DhaTab is due to strong intramolecular H-bonding, which imparts structural rigidity to the material and also improves the planarity of the 2D layers.

Accordingly, the presence of strong intramolecular H-bonding makes the COF structure rigid and flat, which results in the high surface area and crystallinity of the present COF's. This intramolecular H-bonding within the COF also enhances the hydrolytic stability.

In another preferred embodiment, the invention provides a process for the synthesis of hollow spherical COF-DhaTab comprising;

(a) reacting 2,5-dihydroxyterephthalaldehyde (Dha) with a base selected from 1,3,5-tris(4-aminophenyl)benzene (Tab) and $N^1,N^1$-bis(4-aminophenyl)benzene-1,4-diamine (Bad) in a solvent and a mild acid;

(b) sonicating reaction mixture of step (a) to obtain a homogenous dispersion followed by freezing and degassing the dispersion;

(c) heating the dispersion of step (b) to a high temperature for 1 to 3 days to obtain a yellowish orange colored precipitate;

(d) collecting the precipitate of step (c) by purification techniques and washing with a polar solvent to obtain a powder;

(e) subjecting the powder collected in step (d) to solvent exchange with ethanol and drying under vacuum for 24 hours to give a yellowish orange colored powder in 85% isolated yield.

In accordance with the above preferred embodiment, the present invention provides the synthesis of COF's-DhaTab and DhaBad by the Schiff base reaction without a sacrificial template between 2,5-dihydroxyterephthalaldehyde (Dha) and 1,3,5-tris(4-aminophenyl)benzene (Tab) or $N^1,N^1$-bis(4-aminophenyl)benzene-1,4-diamine (Bad) in a combination of mesitylene-dioxane solvent and a catalytic amount of acetic acid. The reactants and solvents are first charged in a pyrex tube and then the mixture subjected to sonication for 10 minutes to obtain a homogeneous dispersion. The tube is flash frozen at 77 K in a liquid $N_2$ bath and degassed by three freeze-pump-thaw cycles. The tube is then vacuum sealed and heated at high temperature ranging from 100° C. to 200° C. and preferably 120° C. for 3 days. A resultant yellow coloured fluffy powder is collected by centrifugation or filtration at the end of the third day and washed with a solvent selected from DMAc, water and ethanol. This yellow powder is dried at 150° C. under vacuum for 12 hours to obtain the corresponding COF in approximately 80% isolated yield.

Self templated hollow sphere formation happens mainly due to the Kirkendall effect and Ostwald ripening. Rod like crystallites of COF-DhaTab and DhaBad synthesized by the present method are formed initially in 12 hours and these crystallites randomly self-assemble into coiled or dense spheres. Since the crystallites in the inner part of the sphere have higher surface energy than those on the outer surface, an inside out Ostwald ripening takes place after 24 hours and hollow spheres of COF-DhaTab and DhaBad are formed. As the time progresses, crystallites on the sphere wall get fused together to produce a smooth surface, thus resulting in the synthesis of the present porous, crystalline, chemically stable and hollow covalent organic frameworks.

In one embodiment the present invention provides highly porous, crystalline, chemically stable and hollow COF's, wherein the COF's retain their spherical morphology in water and phosphate buffer.

Accordingly, this chemical stability and high surface area of the COF-DhaTab arises due to the strong intramolecular hydrogen bonding which locks the phenyl rings in one plane and protects the imine nitrogen from nucleophilic attack. In another embodiment, the present hollow spherical COF (DhaTab), reported in the instant invention is characterized by subjecting the COF to various spectroscopic techniques such as PXRD analysis, FTIR, Scanning electron microscopy (SEM), transmission electron microscopy (TEM) and atomic force microscopy (AFM), Thermo Gravimetric analysis (TGA), these methods aid in detecting the crystallinity, porosity, sphericity and the hollow nature of the present COF's.

Accordingly, the spectroscopic techniques reveal that the present macroporous hollow spherical COF have a spherical core characterized by pore width in the range of 500 nm-2 μm wrapped up by the mesoporous COF shell having width in the range of 20-40 nm. The entire COF-DhaTab assembly of the instant invention is chemically stable and mesoporous having a pore size in the range of 3 to 4 nm. The preferable pore size is 3.7 nm.

Figure 1:
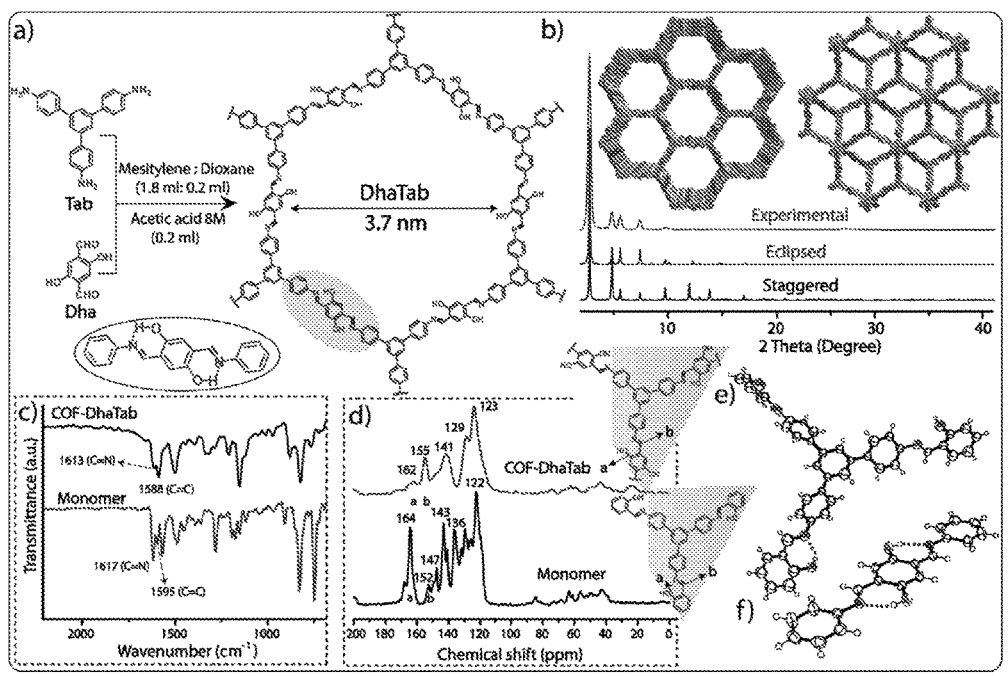
FIG. 1 shows (a) Synthesis of COF-DhaTab by the Schiff base reaction of Tab and Dha. (b) experimental PXRD pattern of DhaTab (red) compared with simulated eclipsed (blue) and staggered (black). (c) Comparison of FTIR spectra of DhaTab (black) with monomer (red). (d) Comparison of solid-state $^{13}C$ NMR spectra of DhaTab (red) with monomer (black). (e) ORTEP diagram of DhaTabtriphynyl core monomer unit. (f) ORTEP diagram of DhaTab linker unit.

The high crystallinity of COF-DhaTab is supported by PXRD analysis, indicated by an intense peak at 2.8° 2θ which corresponds to the 100 plane (FIG. 1b). The π-π stacking distances between the vertically stacked sheets are ~3.4 Å from the d spacing of the 001 planes. This high crystallinity of the present COF-DhaTab is due to the presence of intramolecular O—H...N═C hydrogen bonding between the hydroxyl and imine functional groups, which locks the phenyl rings in one plane and improves the stacking interaction between the adjacent COF layers (FIG. 1a). This improved structural rigidity and planarity of the framework, together with the all trans conformation of the imine bond, results in an increase of the crystallinity of COF-DhaTab.

The effect of H-bonding within the COF architecture was analysed by crystallizing the monomer units 2,2'-[[5'-[4-[[(2-hydroxyphenyl)methylene]amino]phenyl][1,1':3',1"-terphen-yl]-]-4,4"-diyl]bis(nitrilo methylid-yne)] and 2,5-bis((E)-(phenylimino)methyl)-benzene-1,4-diol (FIGS. 1e and 1f) of the COF-DhaTab. Accordingly, the crystal structural determination of the monomer units reveals that the central triphenyl core in COF-DhaTab is not in the same plane as reported for the COF-8, COF-43 and BTP-COF. The phenyl rings within the monomer units are slightly tilted with respect to the central benzene ring in order to avoid the steric repulsion between the hydrogen atoms (FIG. 1(e)). However, the monomer unit that connects one triphenyl core to another to construct the framework (FIG. 1f) is perfectly planar with almost zero dihedral angle between the central and the end phenyl rings. This planarity arises due to strong intramolecular bonding as well as continuous conjugation.

Figure 7:
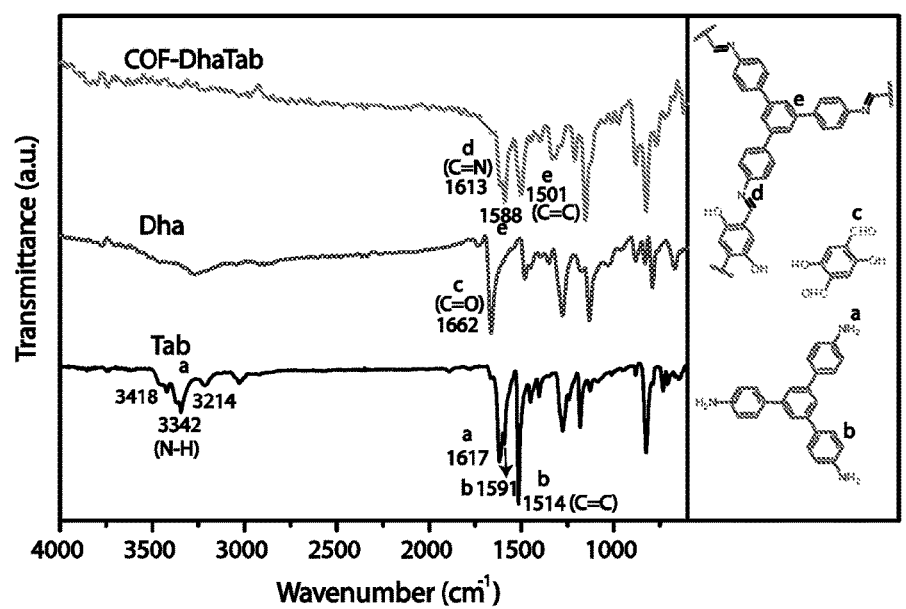
FIG. 7 shows FT-IR spectra of DhaTab (Green), dihydroxyterephthalaldehyde (Dha) (red), and 1,3,5-tris(4-aminophenyl)benzene (Tab) (black)
Figure 8A:
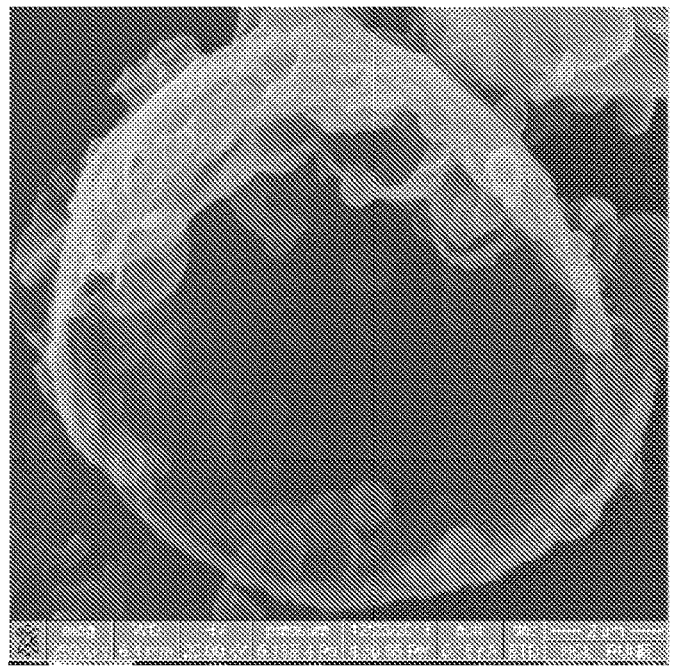
FIGS. 8(a) to 8(f): SEM images of DhaTab
Figure 8B:
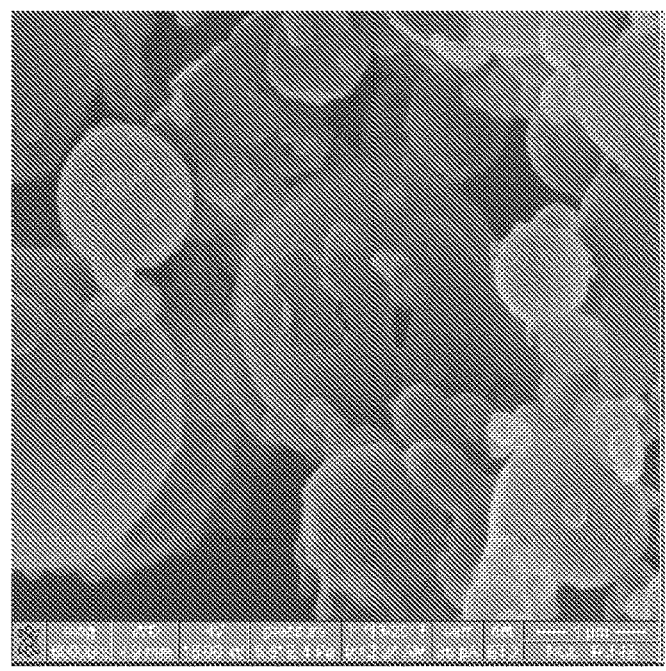
Figure 8C:
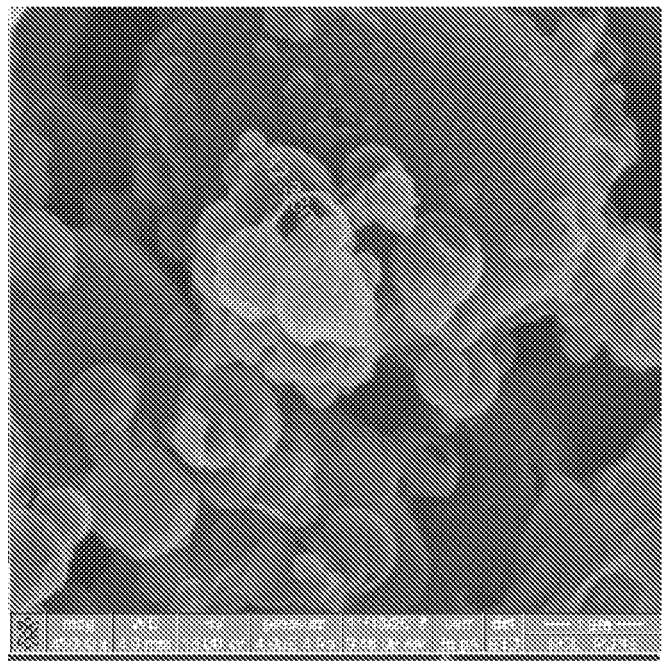
Figure 8D:
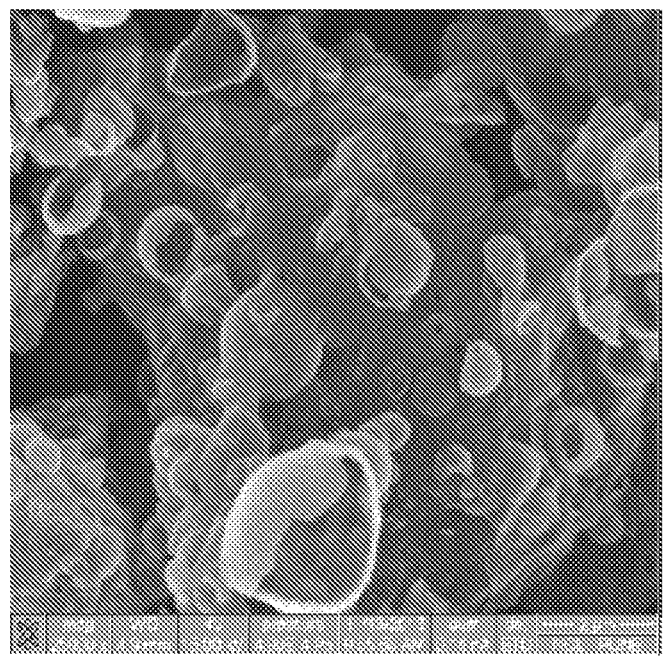
Figure 8E:
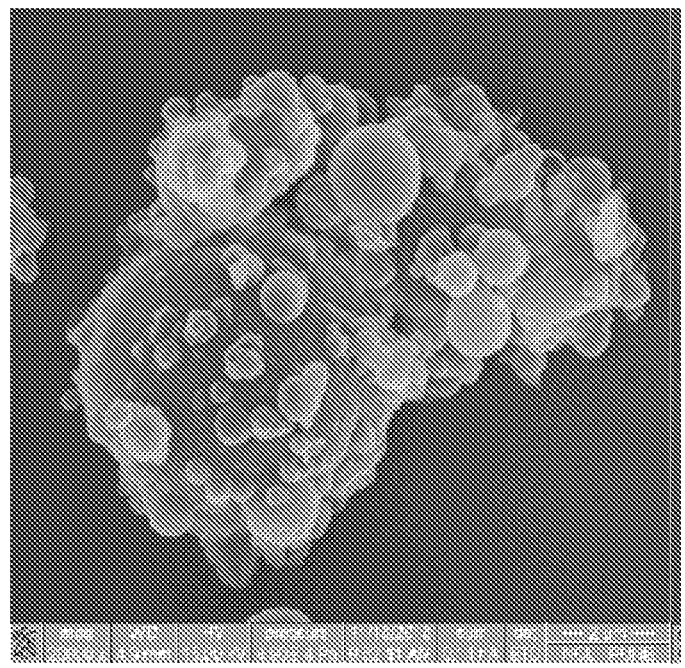
Figure 8F:
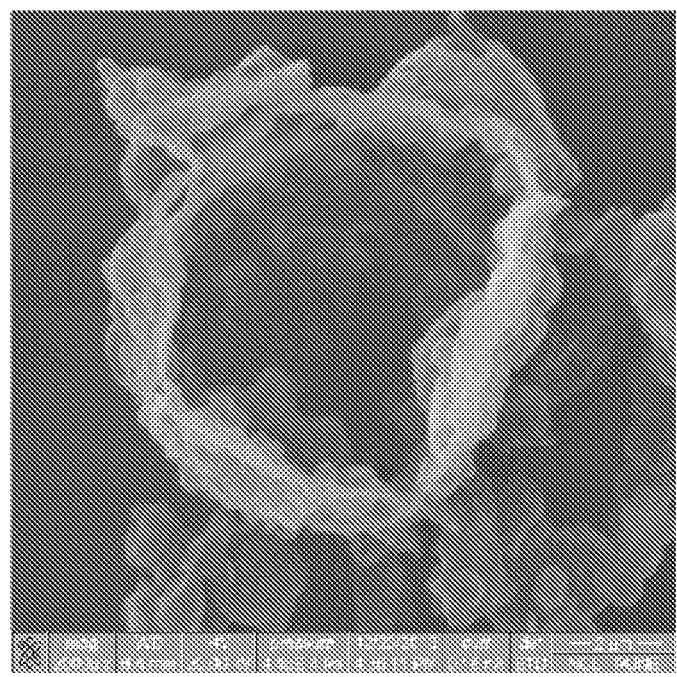
Figure 9A:
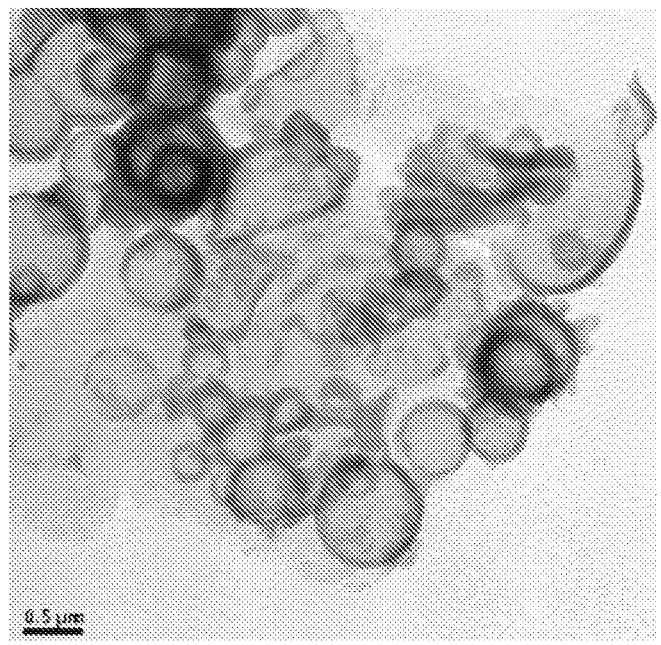
FIGS. 9(a) to 9(f): TEM images of DhaTab
Figure 9B:
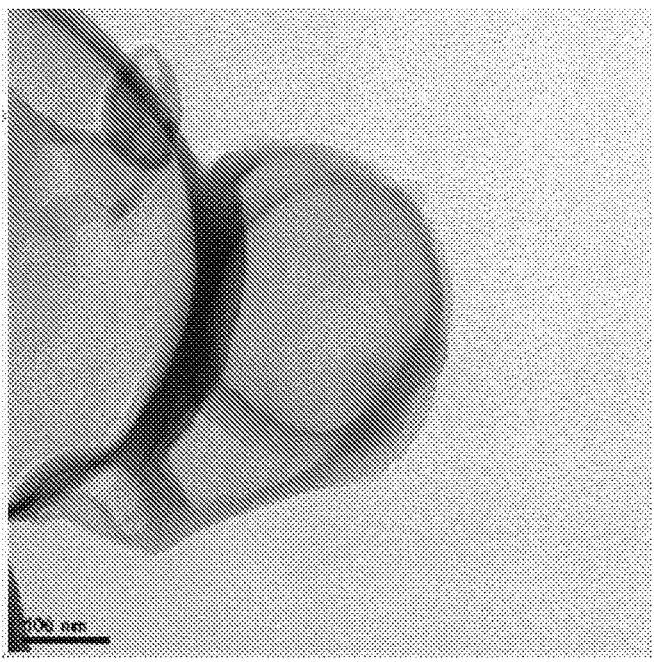
Figure 9C:
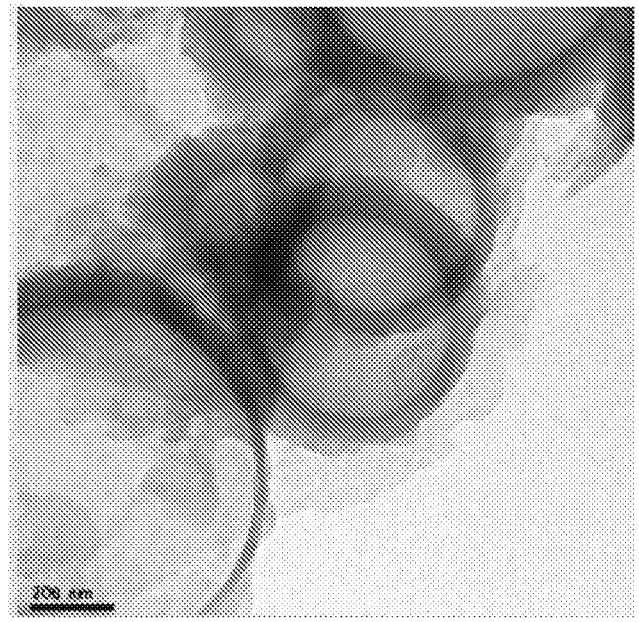
Figure 9D:
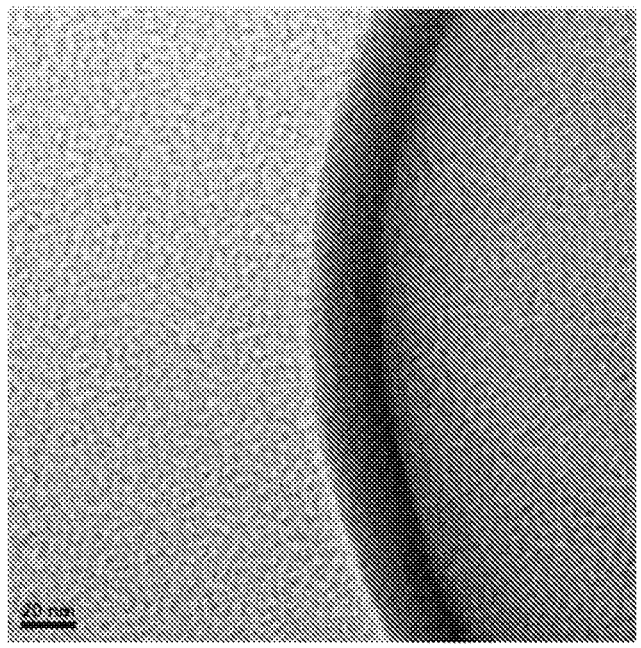
Figure 9E:
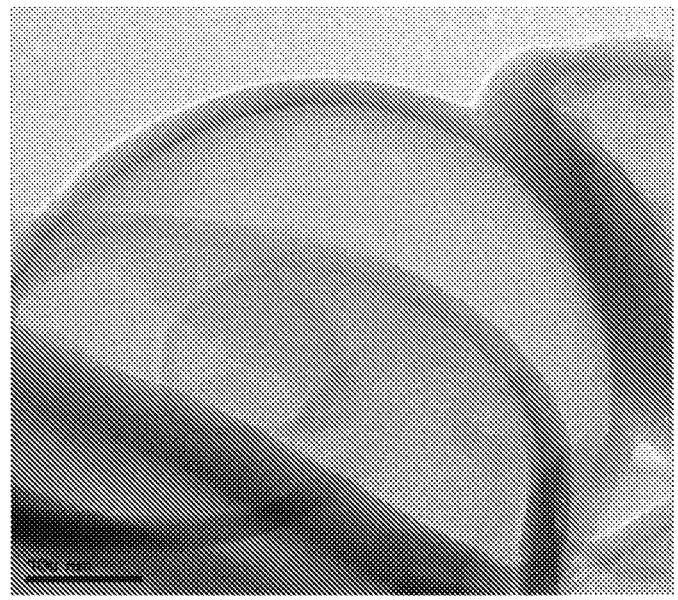
Figure 9F:
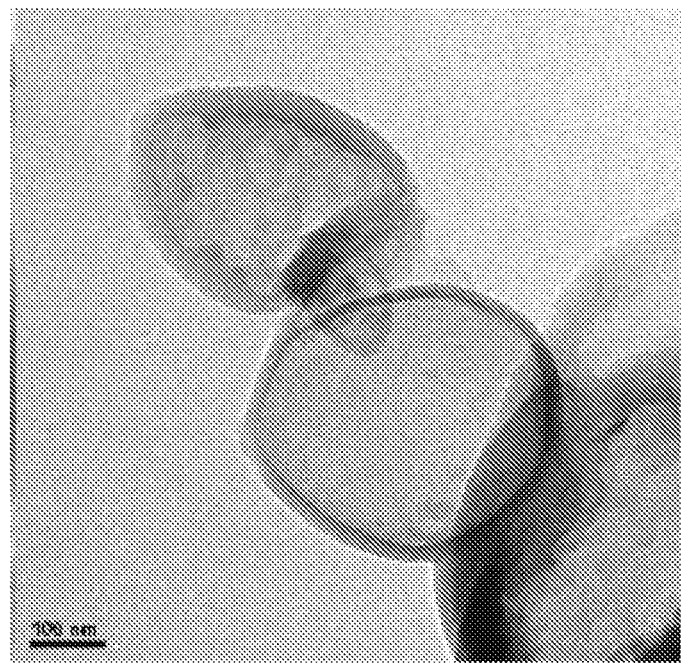
Figure 10A:
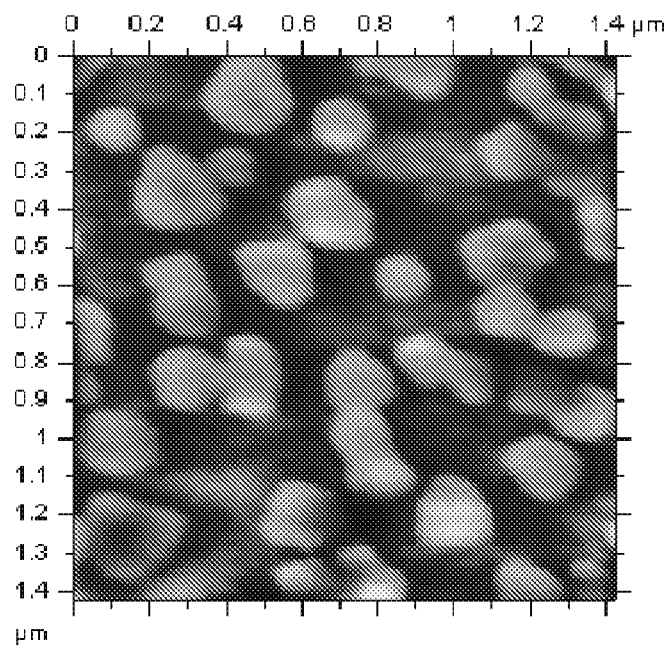
FIGS. 10(a) to 10(f): AFM images of DhaTab
Figure 10B:
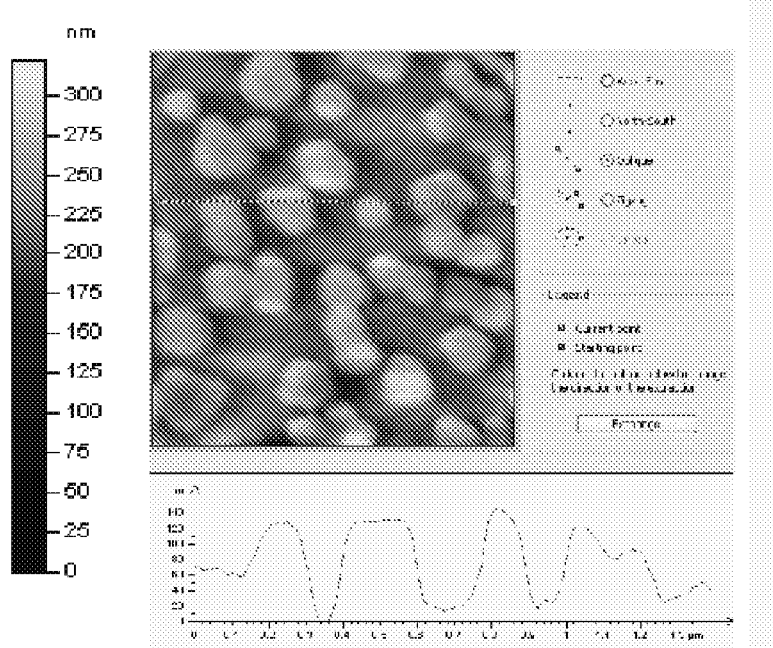
Figure 10C:
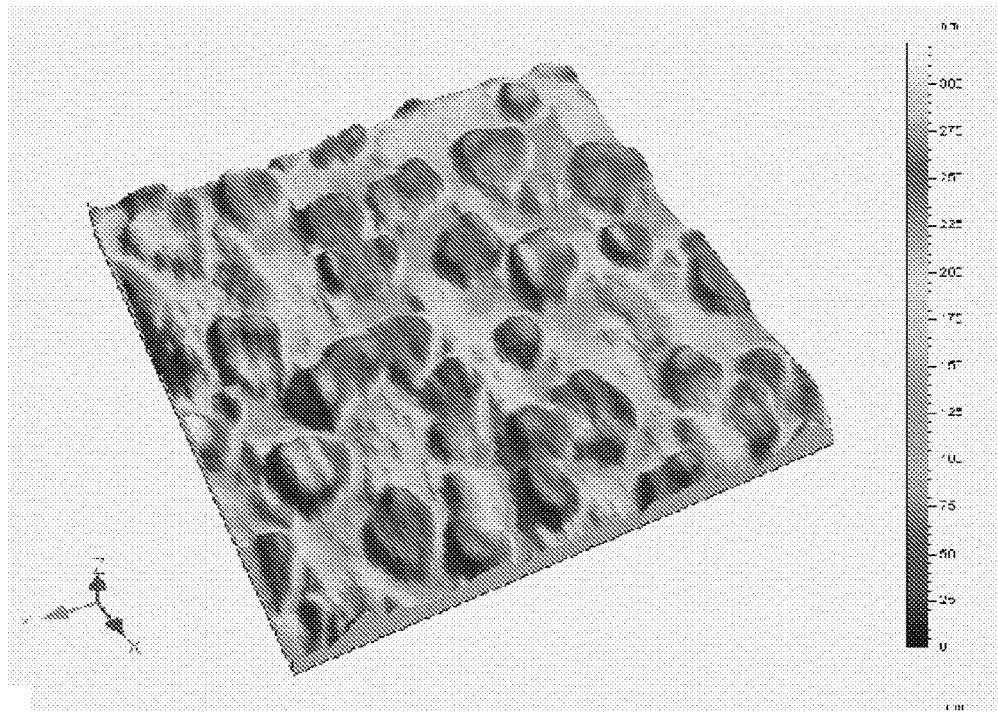
Figure 10D:
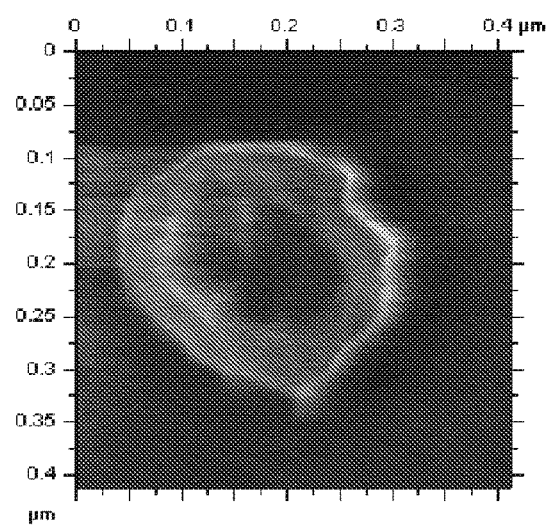
Figure 10E:
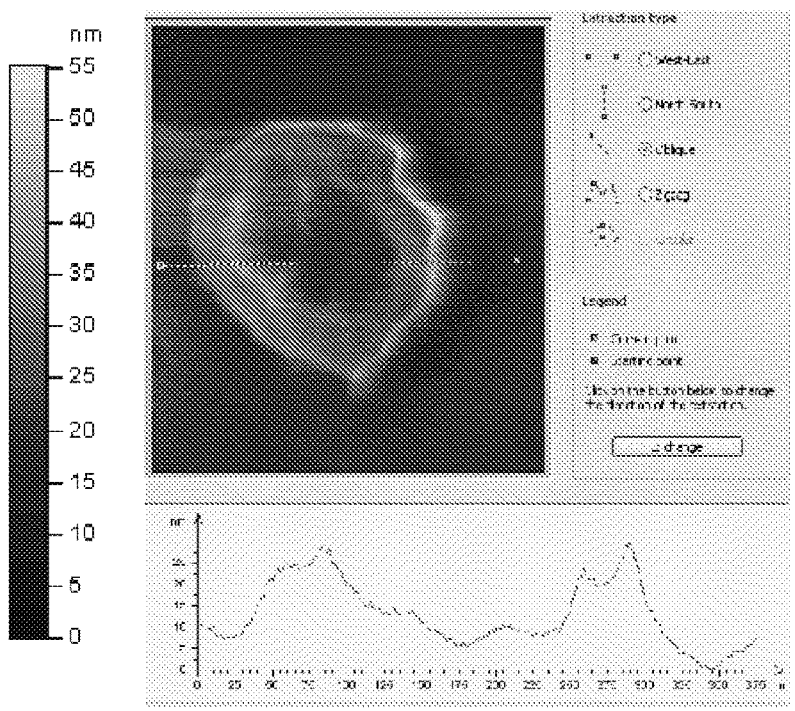
Figure 10F:
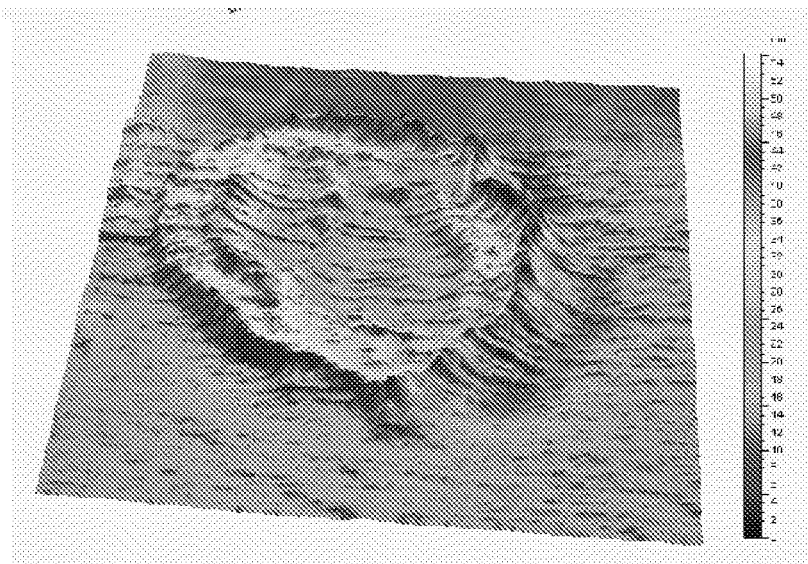
Figure 11A:
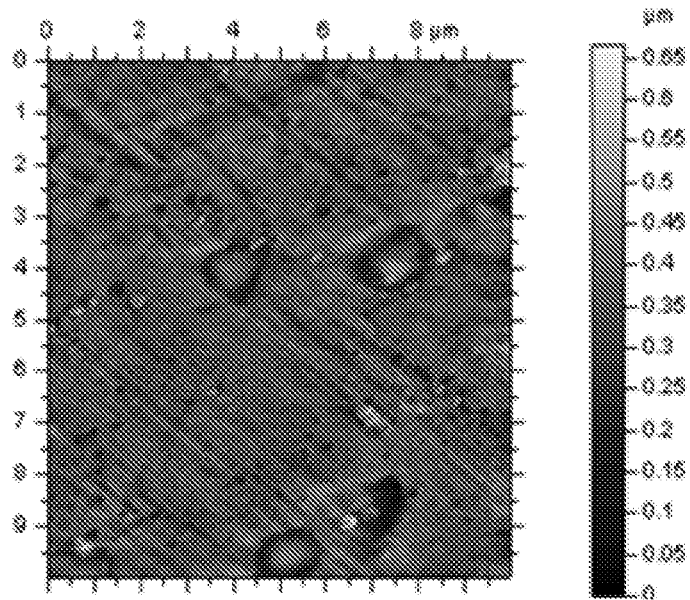
FIGS. 11(a) to 11(d): AFM images of DhaTab
Figure 11B:
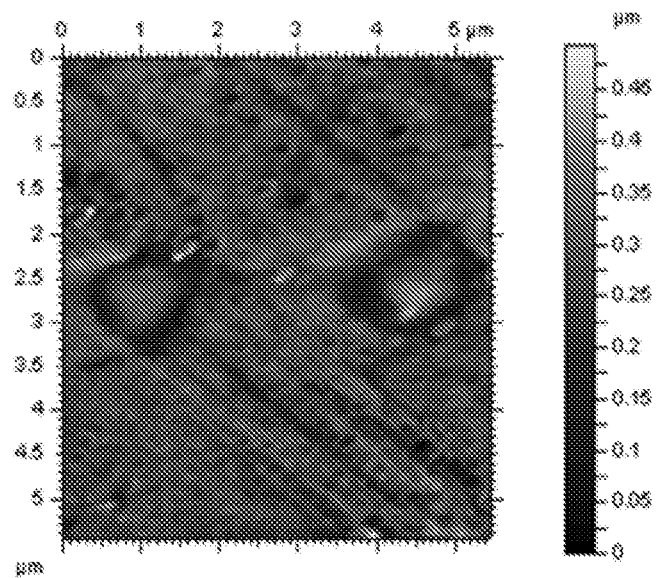
Figure 11C:
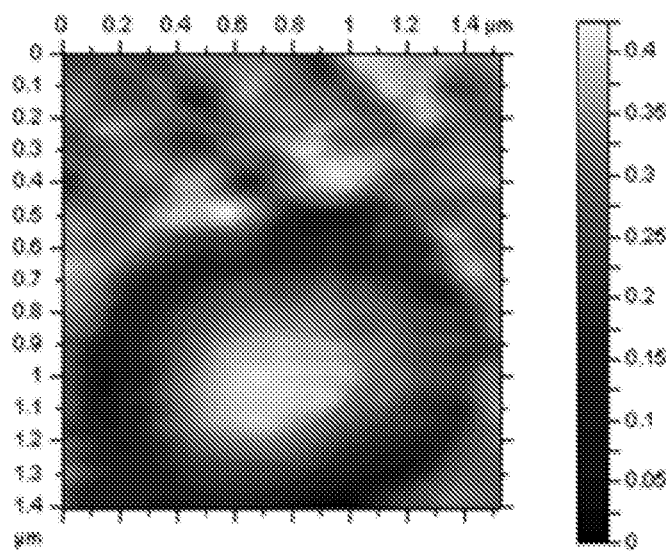
Figure 11D:
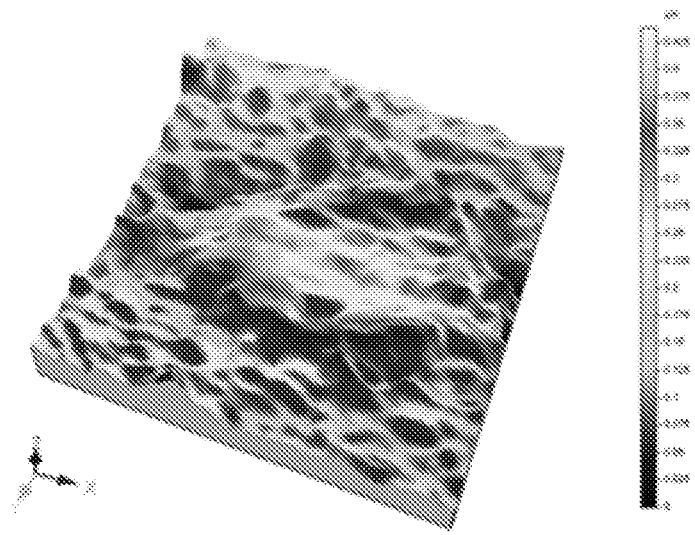

The FT-IR spectra of COF-DhaTab indicates the total consumption of the starting material, as the characteristic —C═O stretching band of Dha and —N—H stretching band of Tab were absent (FIG. 7). The imine bond formation and the existence of COF as the enol form is confirmed from the 13C CP-MAS solid-state NMR spectrum of COF-DhaTab and the corresponding monomer unit (FIG. 1d). This 13C CP-MAS data shows similar location of the imine carbon peak of the COF at 155 ppm with respect to the imine carbon peak of the monomer unit (152 ppm).

SEM images show that DhaTab comprises of a large number of inter-connected hollow spherical particles with average diameter in the range of 0.5-4 μm (FIGS. 2a and 8). Broken walls of some of the spheres resulting during sonication showcase the hollow interior cavity (FIG. 2a). TEM images of the hollow spherical COF-DhaTab show a bright area at the centre of each sphere and a dark contrast at the sphere wall, a characteristic feature of hollow spheres (FIGS. 2b and 9). However, the thickness of the sphere wall is not constant, and varies from 40-80 nm.

Figure 12:
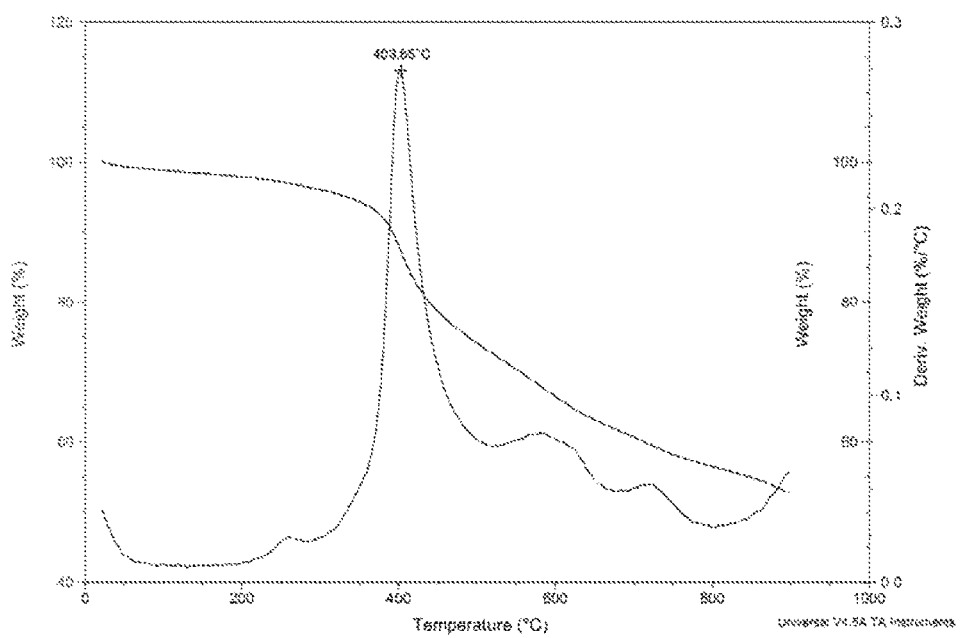
FIG. 12 depicts the TGA data of activated COF DhaTab (72 hrs) under $N_2$ atmosphere.

The spherical morphology of COF-DhaTabparticles was analysed from the AFM images, which shows that the surface of the hollow sphere is smooth. The cross-section analysis revealed that the diameters of the hollow spheres are in the range of 0.5 to 3 μm and the height was measured in the range of 100-150 nm (FIG. 10). This large diameter to height ratio also indicates the hollow nature of the spheres. Certain donut shaped objects while doing the AFM imaging were observed which appear flattened due to the AFM tip during the measuring process (FIG. 11). Thermal stability of the COF-DhaTab hollow spheres was monitored by TGA analysis under $N_2$ atmosphere. The COF framework is found to be stable up to 350° C. without much weight loss. The sharp weight loss of around 45% observed after 400° C. was due to the decomposition of the framework (FIG. 12).

The $N_2$ adsorption was carried out for the activated COF-DhaTab sample in order to evaluate the permanent porosity. COF-DhaTab exhibit reversible type IV isotherm, which is one of the main characteristics of mesoporous materials.

The chemical stability of the hollow spherical COF-DhaTab in water was investigated by submerging the present COF's in water for a week. Retention of peaks in the PXRD pattern and non-alteration of the FTIR peaks after the water treatment shows the structural rigidity of this material in water (FIGS. 2c and 2e). A similar experiment is performed to determine the chemical stability of the COF's in acid. PXRD of the recovered COF-DhaTab samples after acid treatment shows retention of all the main peaks, indicating the retention of the framework structure in the acid treated sample (FIG. 2c). However, a decrease in surface area was observed, which may be due to protonation of the imine nitrogen (FIG. 2d).

Additional stability experiments were performed in phosphate buffer of pH 7.4, since the enzyme encapsulation studies were later performed in the buffer media. Retention of PXRD peaks and unchanged morphology observed from the TEM images confirms the stability of COF-DhaTab in phosphate buffer media (FIG. 2c). In yet another embodiment, the present invention provides the mechanism for formation of the present COF's formed by aggregation of crystallites, leading to the formation of hollow spheres.

Figure 2:
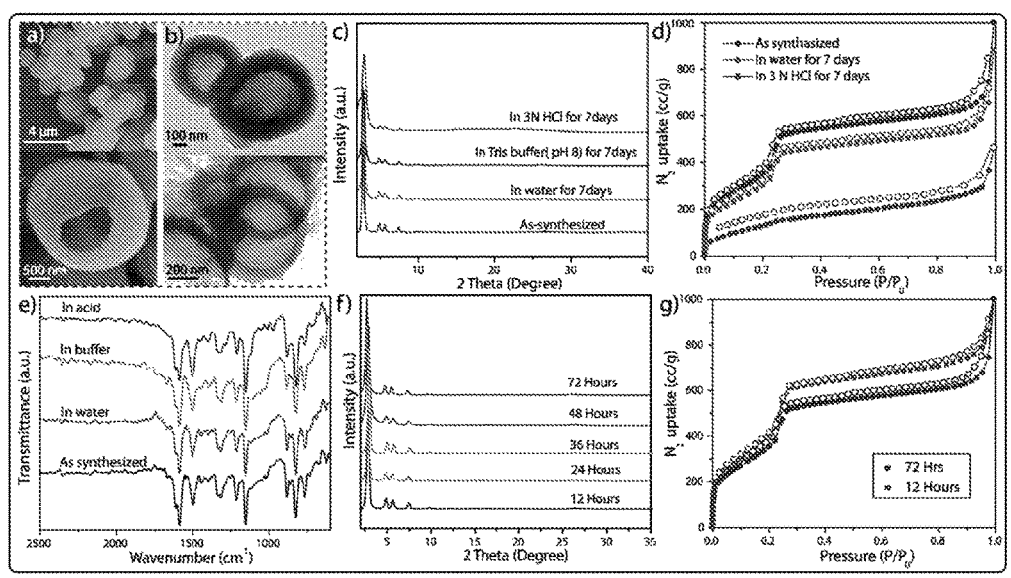
FIG. 2 depicts (a) SEM images of COF-DhaTab hollow spheres. (b) TEM images of COF-DhaTab hollow spheres. (c) PXRD pattern showing the stability of DhaTab. (d) $N_2$ sorption isotherms recorded for DhaTab before (blue) and after water treatment (wine), acid treatment (red) study. (e) FTIR showing the chemical stability of DhaTab. (f) PXRD of DhaTab synthesized at different intervals of time. (g) $N_2$ sorption isotherms recorded for DhaTab synthesized at 12 h (red) and 72 h (blue) intervals of time.
Figure 3:
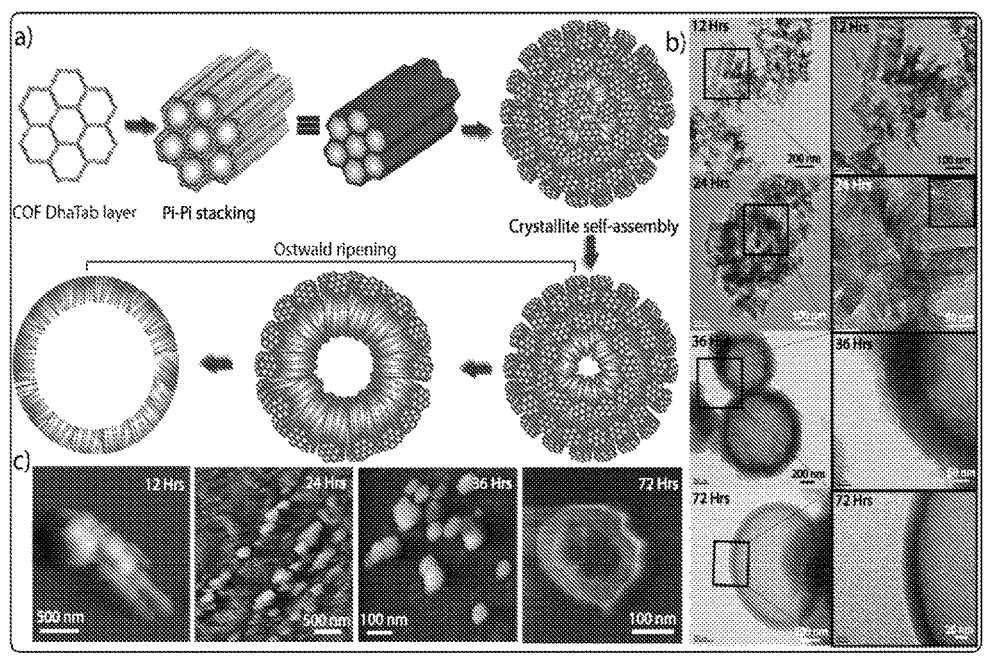
FIG. 3 shows (a) proposed mechanism of the formation of COF hollow spheres. (b) AFM images of COF-DhaTab recorded at different intervals of time. (c) TFM images of COF-DhaTab recorded at different intervals of time.
Figure 19:
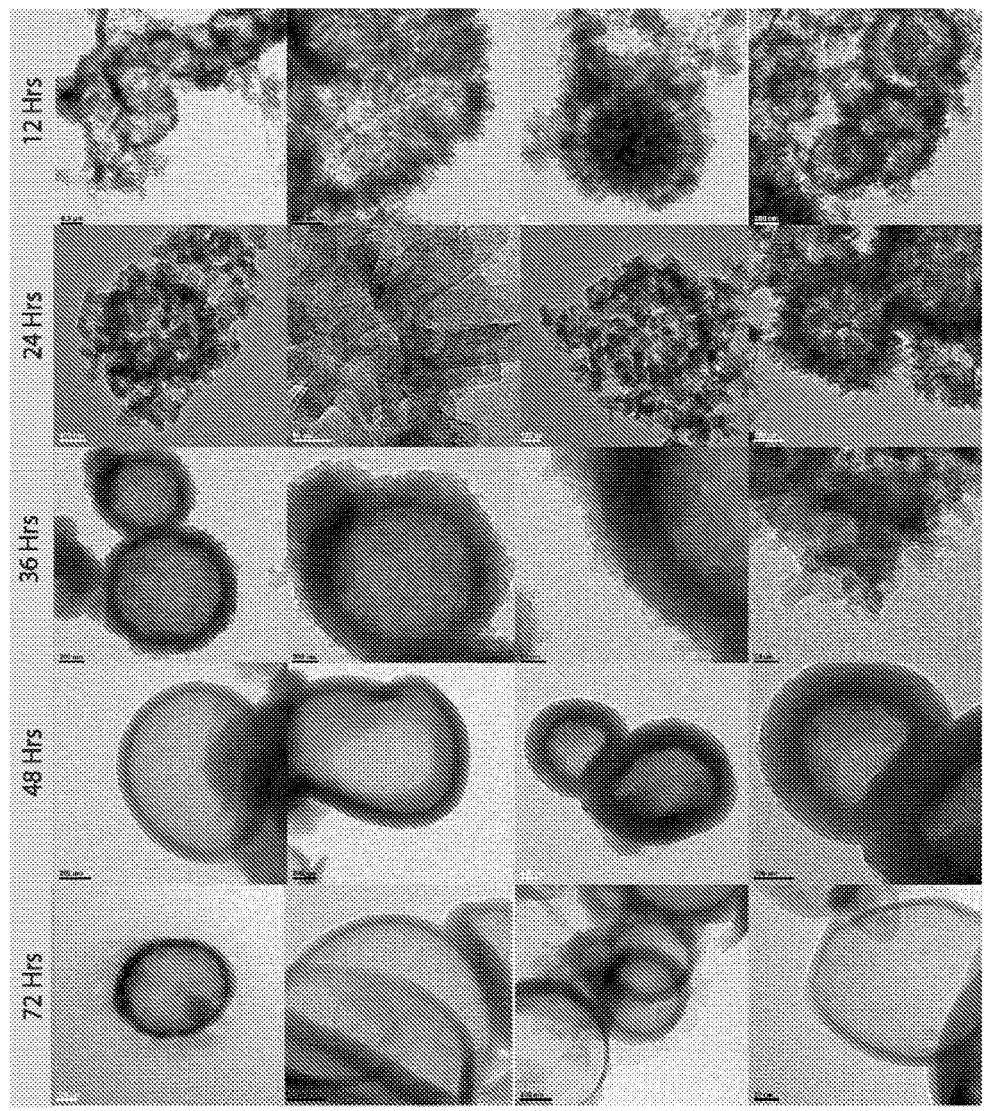
FIG. 19 depicts TEM images of DhaTab synthesized at different intervals of time.

In order to find out the exact mechanism of the hollow sphere formation, the inventors have analysed the COF-DhaTab samples isolated after 12, 24, 36, 48 and 72 h reaction time using microscopic imaging techniques. TEM images of the 12 h sample show rod shaped morphology having lengths in the range 100-150 nm and width in the range 50 nm (FIGS. 3b and 19). After 24 hours, the aggregation of the crystallites becomes more prominent and the morphology becomes more spherical (FIGS. 3b and 19). However, the individual crystallites, which serve as the building units of the hollow spheres, can be clearly seen at the sphere walls under higher magnification. TEM images recorded for COF-DhaTab after a reaction time of 36 hours shows the formation of hollow cavities inside the solid spheres (FIG. 19) as a result of inside out Ostwald ripening. The identical PXRD patterns of the COF-DhaTab samples isolated at different time intervals (12, 24, 36, 48 and 72 hours) show high crystalline nature (FIG. 2f), which indicates that the self-assembly and the Ostwald ripening process of the crystallites does not perturb the internal ordering in the COF.

Further, TEM images recorded at 48 h and 72 h show hollow spherical COF-DhaTab with a smooth sphere surface, which occurs due to the fusion of the crystallites. Since the crystallite surface contains end functional groups they can undergo a Schiff base reaction leading to the formation of a smooth sphere wall surface.

In yet another preferred embodiment, the invention provides hollow spherical COF having mesoporous walls with high surface area for the adsorption and storage of the biomolecules, pharmaceutically important drugs and other biologically and industrially important molecules into the COF pores.

The pharmaceutical drug is selected from the group consisting of doxorubicin, Daunomycin, Mitoxantrone, and Idarubicin. A slow release of around 40% of doxorubicin (DOX) after 7 days in phosphate (pH 5) buffer indicates the potential application of COF hollow sphere for the reversible binding and release of drug molecules.

Biomolecules are selected from the group consisting of enzymes, glycoproteins, essential fatty acids are loaded on the said COF's.

Accordingly, the mesopores of the present COF's facilitate the immobilization of the said biomolecules into the COF pores. In one embodiment, the present invention provides the immobilization of trypsin into the COF-DhaTab pores, wherein the maximum storage capacity of the trypsin for DhaTab was found to be 15.5 µmole.

The macroscopic pores inside the hollow spherical COF-DhaTab can provide greater number of interaction sites for the incoming analyte molecules to interact with the enzyme. It has been observed in conventional techniques used for biomolecule immobilization that microporous materials are not efficient carriers for enzyme immobilization as their pore sizes are too small to fit such large sized biomolecules. In view of the mesoporous property and the chemical stability of the present COF-DhaTab in phosphate buffer and water, the present inventors have performed trypsin adsorption studies in it. Trypsin is a globular protein having hydrodynamic size around 3.8 nm, which is close to the COF-DhaTab pore size (3.7 Å).

According to this embodiment, COF-DhaTab obtained as per the invention was first sonicated in phosphate buffer for 10 minutes in order to get a homogeneous dispersion. This buffer solution was degassed thrice and treated with trypsin and stirred at 4° C. for 24 h in order to absorb the enzyme into the pores of the COF. After 24 h the solution is centrifuged and the absorbance of the decanted solution is measured using UV-Vis spectrometer. The amount of trypsin absorbed in COF-DhaTab is estimated to be 15.5 µmol/g from the absorbance of residual unabsorbed trypsin in the decanted solution.

Figure 4:
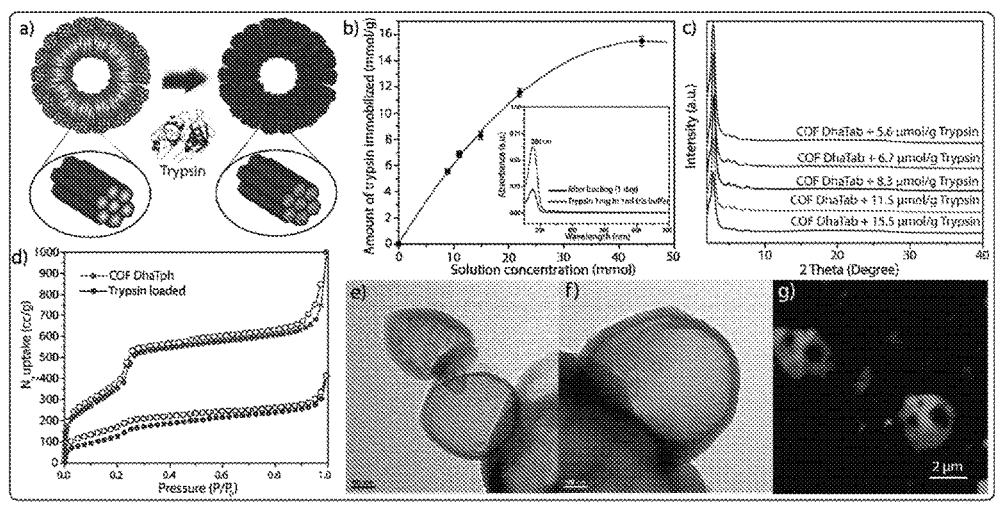
FIG. 4 shows in FIGS. 4(a) and (b) Change in absorbance of the UV-Vis spectra of the trypsin buffer solution before and after adsorption experiments. (c) PXRD powder patterns of DhaTab after the adsorption of trypsin. (d) Comparison of $N_2$ adsorption isotherms DhaTab before and after trypsin loading. (d) Trypsin adsorption isotherm on COF-DhaTph in phosphate buffer (100 mM, pH 7.4) at 4° C. TEM image of DhaTab e) before and f) after enzyme adsorption. (g) Confocal image of Fluorescein labelled trysin loaded DhaTab.
Figure 5:
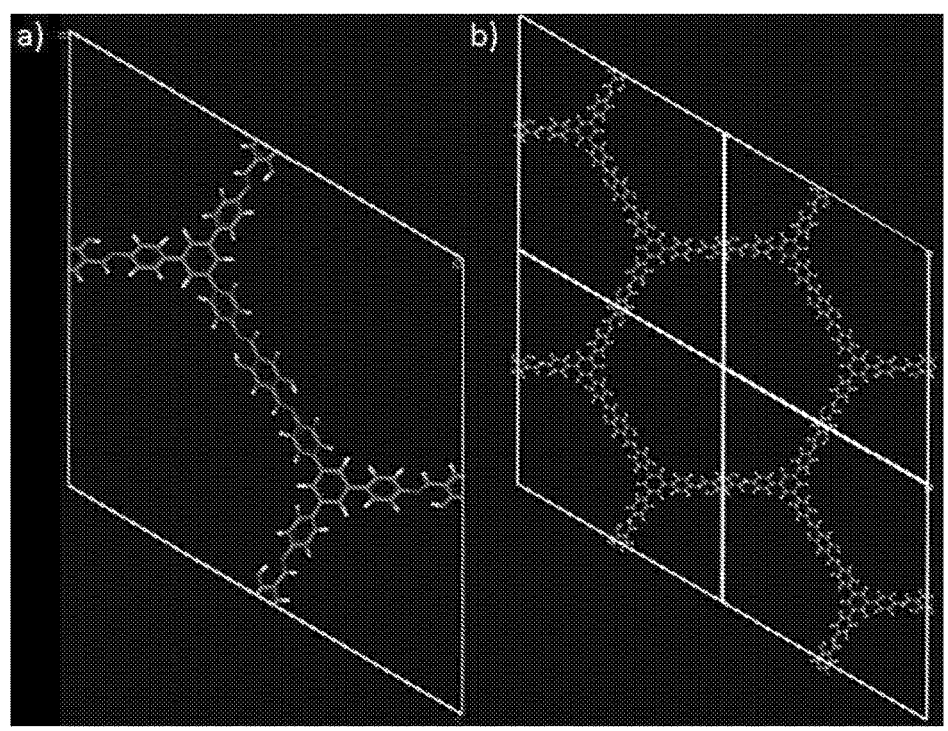
FIG. 5 represents (a) Unit cell and b) Eclipsed crystal lattice packing of COF DhaTab.
Figure 6:
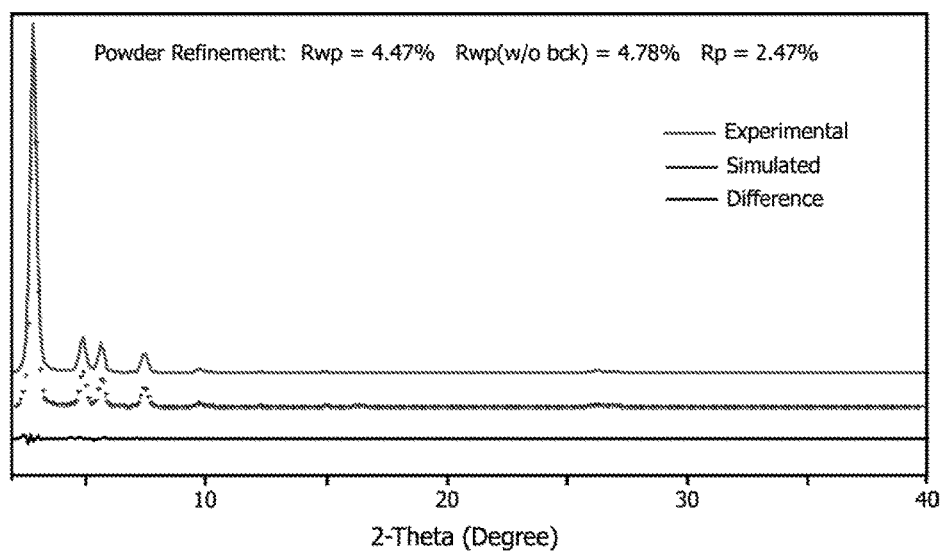
FIG. 6 depicts Experimental (Blue) compared with refined (Red) PXRD profiles of COF-DhaTab with an eclipsed arrangement; difference plot is given in (black)

The present inventors have proved the enzyme adsorption inside the mesopores of COF-DhaTab, by obtaining PXRD and $N_2$ adsorption measurements of the enzyme loaded samples (FIG. 4a). The PXRD peak intensity gradually decreases as the amount of enzyme adsorption in the COF increases thus indicating the presence of enzyme inside the pores of COF, which also decreases the contrast intensity between COF walls and the empty pores. As a result, the peak intensity of the PXRD pattern decreases. Further, the $N_2$ adsorption measurement of the trypsin loaded COF-DhaTab sample shows a decrease in the BET surface area value from 1468 to 400 $m^2g^{-1}$, which also supports the immobilization of trypsin in COF pores (FIG. 4c).

Successful immobilization of trypsin was confirmed by the confocal laser scanning microscopy (CLSM) of the fluorescein labelled trysin loaded COF-DhaTab. The CLSM images shows that the trypsin adsorption happens in the mesoporous walls of the hollow spheres and not in the macroscopic inner hollow cavity of the sphere (FIG. 4g).

Further, the enzymatic activity of the trypsin loaded COF-DhaTab, was indicated by a visual color change from colorless to yellow of the substrate i.e BAPNA (Nα-Benzoyl-D,L-arginine 5-nitroanilide hydrochloride) due to its conversion to p-nitroaniline. The activity was found out to be in the range of 30 to 35 mmol $g^{-1}$ $min^{-1}$.

Further investigations of enzyme immobilized COF as biosensor and biocatalyst is under progress.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Material and Methods:

The hydroxyl aromatic component of the covalent organic framework i.e. 2,5-dihydroxyterephthalaldehyde (Dha) was synthesized by 1,4-dimethoxybenzene according to a previously published procedure by Kretz, T., *Naturforsch.* 62b, 66-74 (2007). Powder X-ray diffraction (PXRD) patterns were recorded on a Rigaku, MicroMax-007HF with high intensity Microfocus rotating anode X-ray generator. All the samples were recorded in the 2θ range of 2-40 degrees and data was collected with the help of Control Win software. A Rigaku, R-axis IV++ detector was employed in wide-angle experiments. The radiation used was CuK (1.54 Å) with a Ni filter, and the data collection was carried out using an Aluminium holder. Fourier transform infrared (FT-IR) spectra were taken on a Bruker Optics ALPHA-E spectrometer with a universal Zn—Se ATR (attenuated total reflection) accessory in the 600-4000 cm$^{-1}$ region or using a Diamond ATR (Golden Gate). Thermo gravimetric analysis (TGA) were carried out on a TG50 analyzer (Mettler-Toledo) or a SDT Q600 TG-DTA analyzer under $N_2$ atmosphere at a heating rate of 10° C. min$^{-1}$ within a temperature range of 30-900° C. SEM images were obtained with a Zeiss DSM 950 scanning electron microscope and FEI, QUANTA 200 3D Scanning Electron Microscope with tungsten filament as electron source operated at 10 kV. The samples were sputtered with Au (nano-sized film) prior to imaging by a SCD 040 Balzers Union. TEM images were recorded using FEI Tecnai G2 F20 X-TWIN TEM at an accelerating voltage of 200 kV. The TEM Samples were prepared by drop casting the sample from isopropanol on copper grids TEM Window (TED PELLA, INC. 200 mesh). All gas adsorption experiments (up to 1 bar) were performed on a Quantachrome Quadrasorb automatic volumetric instrument. Solid state NMR (SSNMR) was taken in a Bruker 300 MHz NMR spectrometer and Ligand NMR data were taken in Bruker 300 MHz NMR spectrometer. Confocal laser scanning microscopy (CLSM) images were taken with Carl Zeiss confocal system equipped with a 20× objective.

Example 2

Synthesis of Hollow Spherical COF-DhaTab:

Synthesis of COF-DhaTab was done by the Schiff base reaction between 2,5-dihydroxyterephthalaldehyde (Dha) (21.6 mg) and 1,3,5-tris(4-aminophenyl)benzene (Tab) (30.2 mg) in mesitylene-dioxane (1.7 mL:0.3 mL) solvent combination and a catalytic amount of 0.2 mL 8 M acetic acid. The reactants and solvents were first charged in a pyrex tube (o.d.×i.d.=12×10 mm$^2$ and length 18 cm) and then the mixture was sonicated for 10 minutes in order to get a homogeneous dispersion. The tube was flash frozen at 77 K (liquid $N_2$ bath) and degassed by three freeze-pump-thaw cycles. The tube was then vacuum sealed and heated at 120° C. for 3 days. A yellow coloured fluffy powder was collected by centrifugation or filtration and washed with DMAc, water and ethanol. This yellow powder was dried at 150° C. under vacuum for 12 hours to get the corresponding COF in ~80% isolated yield.

Example 3

Synthesis of COF-DhaTab at Different Time Intervals:

COF reaction tubes were removed from the oven at different intervals of time (12 h, 24 h, 36 h, 48 and 72 h). After reaching room temperature, the reaction tube was broken and COF powders were thoroughly washed with DMAc, water and ethanol to remove any unreacted starting materials or polymeric side products. The dry powdered samples of DhaTab were used as such for characterization with PXRD, TGA, FT-IR, etc. For TEM, SEM and AFM imaging, 1 mg of DhaTab in 5 mL of isopropanol was sonicated for 10 minutes and subsequently coated on the carbon-coated copper grid (TEM) and Si-wafer or mica (AFM), and dried at room temperature prior to imaging.

Example 4

Loading of Trypsin in COF-DhaTab

For the loading studies, 2 mg of the COF-DhaTab was first sonicated in 2 mL of the phosphate buffer for 10 minutes in order to get a homogeneous dispersion. This buffer solution was degassed thrice and treated with 2 mg of trypsin and stirred at 4° C. for 24 h in order to absorb the enzyme into the pores of the COF. After 24 h the solution was centrifuged and the absorbance of the decanted solution was noted using UV-Vis spectrometer.

Example 5

Structural Characterization of the Present Covalent Organic Frameworks DhaTab

FT-IR spectra of COF-DhaTab indicated the total consumption of the starting material, as the characteristic —C=O (1662 cm$^{-1}$) stretching band of Dha and —N—H (~3300 cm$^{-1}$) stretching band of Tab were absent (FIG. 7). The formation of the imine bond was understood from the FT-IR peak at 1613 cm$^{-1}$, which corresponds to the —C=N stretching and the value appears near to the —C=N stretching band of the monomer unit at 1617 cm$^{-1}$ (FIG. 1c). Similarly, the COF DhaBad exhibited the imine bond (—C=N) stretching at 1607 cm$^{-1}$, which was close to 1611 cm$^{-1}$, the —C=N stretching value of the monomer. The imine bond formation and the existence of COF as the enol form was confirmed from the $^{13}$C CP-MAS solid-state NMR spectrum of COF-DhaTab and the corresponding monomer unit (FIG. 1(d)). This $^{13}$C CP-MAS data showed similar location of the imine carbon peak of the COF at 155 ppm with respect to the imine carbon peak of the monomer unit (152 ppm).

Scanning electron microscopy (SEM), transmission electron microscopy (TEM) and atomic force microscopy (AFM) were used to explore the morphology of the COF-DhaTab particles.

(a) Microscopic Imaging:

SEM images indicate that DhaTab comprises a large number of inter-connected hollow spherical particles with an average diameter of 0.5-4 μm (FIG. 2(a)). Broken walls of some of the spheres which have resulted during sonication showcase the hollow interior cavity. TEM images of the hollow spherical COF-DhaTab showcase a bright area at the centre of each sphere and a dark contrast at the sphere wall, which is one of the main characteristic features of the hollow spheres (FIG. 2b). However, the thickness of the sphere wall is not constant, and varies from 40-80 nm. On the other hand SEM images of the DhaBad depict the morphology of giant hollow spheres, which is formed by the self-assembly of small spheres. From the TEM images it was understood that the smaller spheres are also hollow in nature.

The spherical morphology of COF-DhaTab particles was further understood from the AFM images, which shows that the surface of the hollow sphere is smooth. However, the cross-section analysis revealed that the diameters of the hollow spheres are in the range of 0.5 to 3 μm and the height was measured in the range of 100-150 nm (FIG. 2). This large diameter to height ratio also indicates the hollow nature of the spheres. Since the sphere walls comprise of soft organic material, high local force applied by the AFM tip flattened these hollow spheres. Donut shaped objects while performing AFM imaging supports this flattening of the hollow spheres was also observed (FIGS. 10 and 11).

Thermal stability of the COF-DhaTab and DhaBad hollow spheres was monitored by TGA analysis under $N_2$ atmosphere. The COF-DhaTab framework was found to be stable up to 350° C. without much weight loss. The sharp weight loss (45%) observed after 400° C. was due to the decomposition of the framework, while DhaBad hollow spheres shows thermal stability up to 400° C.

(b) Crystallinity and Structural Determination:

The high crystallinity of COF-DhaTab was revealed from the PXRD analysis, as it shows an intense peak at 2.8° 2θ (intensity around 150000 cps), which corresponds to the 100 plane. The other minor peaks were observed at 4.9, 5.6, 7.4, 9.8, 26.3° 2θ in the PXRD pattern, corresponding to 110, 200, 120, 220, 001 planes respectively (FIG. 1b). The π-π stacking distances between the vertically stacked sheets were calculated to be ~3.4 Å from the d spacing of the 001 plane. The high crystallinity of COF-DhaTab is due to the presence of intramolecular O—H...N=C hydrogen bonding between the hydroxyl and imine functional groups, which locks the phenyl rings in one plane and improves the stacking interaction between the adjacent COF layers (FIG. 1a). This improved structural rigidity and planarity of the framework, together with the all trans conformation of the imine bond, results in the increase of the crystallinity of COF-DhaTab.

In order to understand the effect of H-bonding within the COF architecture, the present inventors have crystallized the monomer units 2,2'-[[5'-[4-[[(2-hydroxyphenyl)methylene]amino]phenyl][1,1':3',1"-terphen-yl]-4,4"-diyl]bis(nitrilomethylid-yne)] and 2,5-bis((E)-(phenylimino)methyl)-benzene-1,4-diol (FIGS. 1e and 1f) of the COF-DhaTab. The crystal structural determination of the monomer units reveals that the central triphenyl core in COF-DhaTab is not in the same plane as reported for the known COF's in the art, i.e. COF-8, COF-43 and BTP-COF. The phenyl rings within the monomer units are a little tilted with respect to the central benzene ring in order to avoid the steric repulsion between the hydrogen atoms (FIG. 1e). However, the monomer unit that connects one triphenyl core to another to construct the framework (FIG. 1f) is perfectly planar with almost zero dihedral angle (θ=0.82° and θ=0.05°) between the central and the end phenyl rings. This planarity arises due the strong intramolecular O—H...N=C H-bonding [D=2.619(2) Å, d=1.895(2) Å, θ=146.68° (3)] as well as continuous conjugation.

A possible eclipsed 2D model for the COF-DhaTab was built using Materials Studio version 6.1, in order to find out the structure and the unit cell parameters. The modeling of COF-DhaTab cannot be done in the conventional P6/m space group since the central triphenyl system is not planar. Hence, we decided to model COF-DhaTab in the P3 space group, with the unit cell parameters a=b=36.2 Å, c=3.4 Å, and α=β=90°, γ=120°. Pawley refinement was performed using the Reflex Plus module of Materials Studio, which showcases good agreement between simulated and experimental PXRD patterns (Rp=2.5%, Rwp=4.5%).

The staggered structure of COF-DhaTab was modeled in R3 space group with the unit cell parameter a=b=36.2 Å, c=10 Å, and α=β=90°, γ=120°. However the simulated PXRD pattern for the staggered conformation has poor matching [Rp=70.5%, Rwp=78%] with the experimental PXRD pattern.

Example 6

Evaluation of Porosity by $N_2$ Adsorption

The $N_2$ adsorption was carried out for the activated COF-DhaTab to evaluate the permanent porosity. COF-DhaTab exhibits reversible type IV isotherm, which is one of the main characteristics of mesoporous materials. The surface area of COF-DhaTab was calculated to be 1480 $m^2g^{-1}$ using the Brunauer-Emmett-Teller (BET) model (FIG. 2(d)). The high surface area of COF-DhaTab as compared with its non-hydroxyl analogue MOP (A-B1) (Xu, C., et al Mater. Chem. A. 1, 3406-3414 (2013)) was due to the presence of strong intramolecular H-bonding, which imparts structural rigidity to the material and also improves the planarity of the 2D layers. This was inferred from the single crystal data of the monomer (FIG. 1(f)) which shows that the three phenyl rings lie in one plane. The improved planarity and structural rigidity facilitated arrangement of the COF layers in an ordered way, which leads to an improvement in crystallinity and surface area. The pore size distribution of COF-DhaTab was calculated using the Barrett-Joyner-Halenda (BJH) desorption model which shows peak maxima at 3.7 nm, and is very close to the theoretically predicted value (3.6 nm). COF-DhaTab shows moderate $H_2$ and $CO_2$ uptake capacity, which was calculated to be 120 $cm^3g^{-1}$ (77 K) and 78 $cm^3g^{-1}$ (273 K) at 1 bar pressure. Surface area of DhaBad was also calculated using the BET method, which shows a moderate value of 447 $m^2/g$. The low surface area of DhaBad as compared with DhaTab was due to its disordered structure.

Example 7

Chemical Stability

The chemical stability of the hollow spherical COF-DhaTab in water was investigated by submerging 30 mg of material in 10 mL water for 7 days. Retention of peaks in the PXRD pattern and non-alteration of the FTIR peaks after the water treatment shows the structural rigidity of this material in water (FIGS. 2c and 2e). $N_2$ adsorption isotherms show that COF-DhaTab remains porous even after prolonged water treatment with a small decrease in the surface area (1480 $m^2g^{-1}$ vs 1220 $m^2g^{-1}$) (FIG. 2d). In addition to that, water vapor adsorption studies of COF-DhaTab were performed, which shows reversible water vapor uptake and confirms the stability of COF in water. Further, elemental analysis of the COF sample was performed before and after the water stability test. It was observed that the elemental weight percentage remains almost identical after the water treatment which indicates the hydrolytic stability of the material. To determine the chemical stability in acid, a similar type of stability experiment was done with 3N HCl for 7 days. PXRD of the recovered COF-DhaTab samples after this acid treatment shows retention of all the main peaks, which indicates the retention of the framework structure in the acid treated sample (FIG. 2c). However, a decrease in surface area was observed, which may be due to protonation of the imine nitrogen (FIG. 2d). The protonation of the imine bond can be understood from the FTIR spectra. In FTIR it was observed that upon treatment of COF-DhaTab with hydrochloric acid a new band arises at 1646 $cm^{-1}$ which indicates the protonation of imine bond (1645 $cm^{-1}$ in monomer. The single crystal data of the protonated Schiff base compound o-(Salicylideneamino) phenol shows that imine bonds are susceptible to protonation upon treatment with hydrochloric acid. $^1H$ NMR studies of the monomer shows that there is a shift in the position of the —OH proton upon hydrochloric acid treatment. This can be due to the loss of intramolecular hydrogen bonds up on protonation of imine bonds. Additional stability experiments were performed in a phosphate buffer of pH 7.4, since the enzyme encapsulation studies were later performed in the buffer media. Retention of PXRD peaks and unchanged morphology observed from the TEM images confirms the stability of COF-DhaTab in phosphate buffer media (FIG. 2c).

Further, hydrothermal stability of COF-DhaTab at different temperatures (40° C., 60° C. and 80° C.) for 24 h was also determined. The unaltered PXRD and FTIR pattern confirm the hydrothermal stability of the material. COF-DhaTab was found to be unstable under basic conditions (3N NaOH). The chemical stability of COF-DhaTab was due to the presence of the intramolecular O—H...N=C hydrogen bonding, which protects the imine bond from the attack of the nucleophiles. Treatment with NaOH caused the removal of the phenolic (—OH) hydrogen which is responsible for hydrogen bonding. Absence of this intramolecular O—H...N=C hydrogen bonding and the presence of $Na^+$ ion near to the phenolate anion present in different COF layers disturbs the ordered layer stacking, which may cause the disintegration of COF-DhaTab hollow spheres. To prove this dynamic light scattering (DLS) study of the leached out sample was performed, which shows the presence of particle having size less than 10 nm, which is very small as compared to the size of the COF hollow spheres. SEM imaging of the COF DhaTab sample before and after treatment shows that the hollow sphere morphology of the COF-DhaTab was lost after the base treatment and the morphology transforms into aggregated platelet like structure. These results indicate that the hollow sphere morphology of COF-DhaTab get disintegrated into small particles in the presence of NaOH which may be the reason for the loss of crystallinity of DhaTab during NaOH treatment.

Example 8

Synthesis and morphological changes in COF-DhaTab at different time intervals (12, 24, 36, 48 and 72 h) were analysed. COF-DhaTab synthesis was quenched by removing the reaction pyrex tubes from the oven at those specific time intervals. Thereafter, the COF-DhaTab samples isolated after 12, 24, 36, 48 and 72 h reaction time were comparatively analysed for their structural and chemical properties by FT-IR, NMR, TGA, PXRD, $N_2$ adsorption and elemental analysis. Identical PXRD patterns of the COF-DhaTab samples synthesized at different time intervals (12, 24, 36, 48 and 72 h) (FIG. 2(f)), indicates that COF crystallite formation is complete even at shorter reaction time.

The COF-DhaTab samples synthesized at shorter reaction time i.e. at 12 hours depicts identical FT-IR, $^{13}C$ CP-MAS and $N_2$ adsorption isotherm (1536 and 1480 $m^2g^{-1}$), which is an extremely important observation and rarely observed in COFs (FIG. 2(g)). This observation indicates that large scale synthesis of good quality COFs is possible in a shorter reaction time, a phenomenon similar to its inorganic counterpart MOFs. Similarly, thermal stability of COF-DhaTab samples synthesized at different time intervals (12, 24, 48 and 72 h) was monitored by TGA analysis under $N_2$ atmosphere, and showed almost identical behaviour (stable up to 350° C.).

Example 9

Mechanism of Hollow Sphere Formation

The exact mechanism of the hollow sphere formation was deciphered by analysing the COF-DhaTab samples isolated after 12, 24, 36, 48 and 72 h reaction time using TEM, SEM and AFM imaging. TEM images of the present COF's are depicted in FIG. 19 show rod shaped morphology having length in the range 100-150 nm and width in the range 50 nm (FIG. 3(b)). These crystallites were formed by the π-π stacking of COF layers along the c axis, as indicated by the simulated crystal structure in FIG. 3(a). The hexagonal pores of the DhaTab with regular pore channels in the crystallites were viewed along a and b axes (FIG. 3(b)). As the reaction progressed, crystallites were self-assembled into various shapes, including coiled and dense spherical structures. After 24 h, the aggregation of crystallites became more prominent and morphology more spherical. However, individual crystallites, which served as building units of hollow spheres, were clearly seen at the sphere walls under higher magnification. TEM images recorded for COF-DhaTab after 36 h showed hollow cavity formation inside solid spheres due to inside out Ostwald ripening. The identical PXRD patterns of the COF-DhaTab samples isolated at the said different time intervals show high crystalline nature (FIG. 2f), which indicated that the self-assembly and the Ostwald ripening process of the crystallites does not perturb the internal ordering in the COF. Although the phenomenon of Ostwald ripening was well explained as a cause of hollow sphere formation in inorganic metal oxides, in organic and polymer based hollow spheres this phenomena is rarely seen, since most of them are amorphous in nature. The purpose of inside out Ostwald ripening was to minimize surface energy of the system. The crystallites in the inner part of the sphere have higher surface energy compared to the crystallite in the outer surface, since they have got higher curvature, being arranged in spheres of smaller radius. To minimize the surface energy, crystallites redissolve or migrate from the inner core and get recrystallized/self assemble at the outer walls of the spheres. However, the wall of the hollow sphere formed at 36 h is not smooth and the rod like crystallite projections can be seen in the TEM image under higher magnification (FIG. 3b). The TEM images recorded at 48 h and 72 h show hollow spherical COF-DhaTab with a smooth sphere surface, which may have happened due to the fusion of the crystallites. Since the crystallite surface contains end functional groups (amine or aldehyde), they can undergo a Schiff base reaction leading to the formation of a smooth sphere wall surface. As mentioned already, the crystallinity and PXRD peak intensity of COF-DhaTab samples, isolated after the 12 h reaction time, remain identical. This shows that crystallization and growth of the COF-DhaTab crystallites are complete within a shorter reaction time (12 h) and after that, self-assembly of the crystallites occurs, which finally leads to the unprecedented phenomenon of this chemically stable COF hollow sphere formation. This observation was supported by the TEM images at different time intervals: it was found that the size of COF crystallites synthesized at 24 and 36 h remains almost identical to that of the 12 h sample. However a small decrease (4%) in surface area was observed for the COF-DhaTab synthesized at 72 h compared to the 12 h sample. This change may be probably due to the fusion of the crystallite after 72 h.

FT-IR, $^{13}C$ CP-MAS and TGA analysis of the COF-DhaTab sample isolated at different time shows identical nature indicating that chemical compositions are the same for 12 h and 72 h COF samples. In order to understand the effect of reaction conditions on the evolution of the hollow spheres, COF-DhaTab in different solvent combinations were synthesized such as a) mesitylene:dioxane-1:1, b) mesitylene:dioxane-1.3:0.7, c) mesitylene:dioxane-1.7:0.3, d) mesitylene:dioxane-2:0 and at different temperature (80° C., 100° C. and 120° C.). From the TEM images it was understood that hollow sphere formation is more favorable in low concentrations of the dioxane (mesitylene:dioxane-2:0 and 1.7:0.3). When the concentration of dioxane increases, (at mesitylene:dioxane-1.3:0.7 and 1:1) the count of hollow spheres observed in the sample starts decreasing and with distorted spherical morphology. The possible reason for this phenomenon is due to the water in oil type behavior of mesitylene-dioxane 2:0 or 1.7:0.3 system. TEM images of the COF-DhaTab sample synthesized at three different temperatures (80° C., 100° C. and 120° C.) shows the hollow sphere formation. But at 80° C., along with hollow spheres some dense spherical structures were also observed. Additionally, a new imine based COF (DhaBad) was also synthesized by using starting materials 2,5-dihydroxyterephthalaldehyde (Dha) and $N^1,N^1$-bis(4-aminophenyl)benzene-1,4-diamine (Bad) in mesitylene:dioxane (1.7:0.3 mL) solvent combination. In this case hollow spheres were formed by the self assembly of the microspheres. The mechanism of hollow sphere formation in DhaB ad at different time intervals was analysed (12 h, 36 h, 72 h). It was found that in the initial 12 h, DhaBad were evolved as particles of spherical morphology. As the time progresses, these small spheres self assemble into various shapes like fibers and particles with curved surface etc (36 h). At 72 h complete hollow sphere formation was observed.

Example 10

Enzyme Adsorption

The immobilization of biomolecules such as enzymes in mesoporous materials improves the recyclability of expensive proteins, and mainly enhances its stability under extreme conditions, therefore immobilization constitutes and important research area in biomedical and pharmaceutical industries. However, such microporous materials do not serve as appropriate alternatives for enzyme immobilization due to their small pore sizes which are not conducive to affix large sized biomolecules. The presently synthesized COF-DhaTab is mesoporous in nature and has chemical stability in phosphate buffer and water, the present inventors have studied and analysed enzyme adsorption i.e. trypsin adsorption into covalent organic frameworks. Trypsin is a globular protein having hydrodynamic size around 3.8 nm, which is close to that of COF-DhaTab pore size (3.7 Å). This approximate identity in the relative size does not affect the trypsin adsorption in COF pores, since enzymes are soft molecules and can adjust their conformation to fit inside the COF pores. The amount of trypsin absorbed in COF-DhaTab was estimated to be 15.5 $\mu molg^{-1}$ from the absorbance of residual unabsorbed trypsin in the decanted solution.

In order to prove the enzyme adsorption inside the mesopores of COF-DhaTab, the PXRD of the enzyme loaded samples (FIG. 4a) was recorded and it was found that the PXRD peak intensity gradually decreases as the amount of enzyme adsorption in the COF increases. This indicates the presence of enzyme inside the pores of COF, which will decrease the contrast intensity between COF walls and the empty pores.

As a result, the peak intensity of the PXRD pattern decreases. $N_2$ adsorption measurement of the trypsin loaded COF-DhaTab sample shows a decrease in the BET surface area value (from 1480 to 400 $m^2g^{-1}$, which also supports the immobilization of trypsin in COF pores (FIG. 4c). Successful immobilization of trypsin was confirmed by the confocal laser scanning microscopy (CLSM) of the fluorescein labeled trypsin loaded COF-DhaTab. The CLSM images show that the trypsin adsorption happens in the mesoporous walls of the hollow spheres and not in the macroscopic inner hollow cavity of the sphere (FIG. 4g). While moving from sphere wall to the centre of the hollow sphere, fluorescent intensity gets decreased considerably which indicates that the inner part of the hollow sphere, contains a very small amount of enzyme. The interaction between the nanometer (3.8 nm) sized enzyme and the micrometer sized inner voids is not feasible, as there is a large difference in the size ratio of the guest and host. However, the inner empty space in the hollow spheres can provide a greater area of interaction sites for the incoming analyte molecules. TEM images of the trypsin loaded samples show that the hollow sphere morphology remains intact even after the loading process (FIGS. 4e and 4f). The retention of enzymatic activity after the immobilization of enzyme is an important feature, since in many cases after the immobilization process the enzyme loses its activity, either due to conformational change, or by the hindrance of the catalytically active site. In order to find out the enzymatic activity of the trypsin loaded COF-DhaTab, the sample was treated with 2 mM N-Benzoyl-L-arginine 4-nitroanilide (BAPNA) in tris buffer (50 mM, pH 8) for 30 minutes. The visual color change from colorless to yellow (due to the hydrolysis of BAPNA to p-nitroaniline) indicates that the activity of the enzyme was retained in the trypsin loaded COF-DhaTab and the activity was found out to be 56.5 mmol $g^{-1}$ $min^{-1}$ which is about 60% of the activity of the free enzyme. The enzyme loading capacity of the COF-DhaTab and the catalytic activity of the enzyme loaded COF is comparable to other literature reported values.

Example 11

Drug Adsorption into COF Pores

Additionally, in the COF hollow sphere, the loading and release study of the anticancer drug doxorubicin (DOX) was performed. The amount of DOX was loaded in COF was calculated as 0.35 mg/g. The drug release profile shows a slow release of DOX (42%) after 7 days in phosphate (pH 5) buffer. This result indicates the potential of using the COF hollow sphere for the reversible binding and release of drug molecules.

Results:

The present invention report the synthesis of a chemically stable hollow spherical COF (DhaTab) having mesoporous walls with high surface area (1500 $m^2$ $g^{-1}$) and chemical stability via self-templated synthesis. Self-templated synthetic methods[1a-b] are considered to be the most cost effective synthetic methods for hollow sphere synthesis, since they don't need any sacrificial templates. Template free methods also avoid problems such as inevitable shell collapse and the contamination of pores during the template removal.[2] Although self templating has been the major recipe for the synthesis of metal oxide and metal sulfide based hollow spheres,[2] this method has been less explored to synthesize organic and polymer based hollow spheres. The hollow spherical COF (DhaTab), reported in this paper, consists of a macroporous inner cavity [pore width 500 nm-2 μm] wrapped up by the mesoporous COF shell [width 20-40 nm]. It is noteworthy that the application of COFs are still mostly limited to the storage of gas molecules, since most of the COFs synthesized are microporous in nature and their pores are not large enough to hold the bigger molecules like drugs or enzymes. Even though few mesoporous boronic acid based COFs have been reported in the literature[3] their chemical instability prevents the usage of these materials for the storage of drugs and enzymes.[4] Since the COF-DhaTab is chemically stable and mesoporous (3.7 nm), we have decided to study the adsorption and storage of the enzyme trypsin into the COF pores. Immobilization of enzyme into the mesoporous material is very useful for applications like biosensors and biocatalysts because it helps to increase the recyclability of the costly enzyme and also improves the stability of enzymes under extreme conditions. The maximum storage capacity of the trypsin for DhaTab was found to be 15.5 μmol/g. These results could lead to an initiation of the detailed investigation of COF crystallite formation and their self assembly. We believe that the macroscopic pores inside the hollow spherical COF-DhaTab can provide greater number of interaction sites for the incoming analyte molecules to interact with the enzyme. Further investigations of this enzyme immobilized COF as biosensor and biocatalyst is under progress. Isoreticulation of the mesoporous COFs with intramolecular hydrogen bonding sites, and their size selective enzyme adsorption studies are also under investigation.

REFERENCE 1) (a) Yun, G.; Hassan, Z.; Lee, J.; Kim, J.; Lee, N. S.; Kim, N. H.; Baek, K.; Hwang, I.; Park, C. Y.; Kim, K, *Angew. Chem., Int. Ed.* 2014, 53, 6414. (b) Yin, Y.; Rioux, R. M.; Erdonmez, C. K.; Hughes, S.; Somorjai, G. A.; Alivisatos, A. P. *Science* 2004, 304, 711.
2) Hu, J.; Chen, M.; Fang, X. S.; Wu, L. M. *Chem. Soc. Rev.* 2011, 40, 5472.
3) Spitler, E. L.; Koo, B. T.; Novotney, J. L.; Colson, J. W.; Uribe-Romo, F. J.; Gutierrez, G. D.; Clancy, P.; Dichtel, W. R. *J. Am. Chem. Soc.* 2011, 133, 19416.
4) Lanni, L. M.; Tilford, R. W.; Bharathy, M.; Lavigne, J. J. *J. Am. Chem. Soc.* 2011, 130, 11872.

Advantages of Invention

Template free and Economical process
Stable spheres are synthesized
Spheres have high surface area
Immobilization of biomolecules into the mesoporous material has potential application in biosensors and biocatalysts because it helps to increase the recyclability of expensive enzymes and also improves the stability of enzymes under extreme conditions
The macroscopic pores inside the hollow spherical COF-DhaTab can provide greater number of interaction sites for the incoming analyte molecules to interact with the enzyme.
Isoreticulation of the mesoporous COFs with intramolecular hydrogen bonding sites, and their size selective enzyme adsorption studies.

The invention claimed is:

1. A hollow, spherical covalent organic framework (COF) comprising an imine formed by reaction of 2, 5-dihydroxyterephthalaldehyde (Dha) and 1, 3, 5-tris(4-aminophenyl)benzene (Tab) or N1,N1-bis(4-aminophenyl)benzene-1,4-diamine (Bad), wherein the imine formed by reaction of Dha and Tab is Dha-Tab, and the imine formed by reaction of Dha and Bad is Dha-Bad.

2. The covalent organic framework according to claim 1, wherein the COF is characterized by an inner cavity having a pore width in the range of 500 nm-2000 nm and a wall thickness in the range of 20 nm-40 nm.

3. The covalent organic framework according to claim 1, wherein the COF comprises mesopores having a pore size in the range of 3.5 nm-4 nm.

4. The covalent organic framework according to claim 1, wherein the diameter of the COF is in the range of 0.5 to 3 μm.

5. The covalent organic framework according to claim 3, wherein a biomolecule is immobilized into the COF's mesopores.

6. The covalent organic framework according to claim 5, wherein the biomolecule is selected from the group consisting of an enzyme, a glycoprotein, and an essential fatty acid.

7. The covalent organic framework according to claim 6, wherein the biomolecule comprises the enzyme, and wherein the enzyme comprises trypsin.

8. The covalent organic framework according to claim 7, wherein the trypsin is immobilized into the COF's mesopores at a concentration ranging from 15-20 μmole per gram.

9. The covalent organic framework according to claim 1, wherein an antineoplastic pharmaceutical is immobilized on the COF.

10. The covalent organic framework according to claim 9, wherein the antineoplastic pharmaceutical is selected from the group consisting of doxorubicin, Daunomycin, Mitoxantrone, and Idarubicin.

11. The covalent organic framework according to claim 1, wherein a gas is adsorbed on the COF.

12. A process for synthesis of the hollow, spherical covalent organic framework of claim 1 comprising:
(a) reacting 2,5-dihydroxyterephthalaldehyde (Dha) with a base selected from 1, 3, 5-tris(4-aminophenyl)benzene (Tab) and N1,N1-bis(4-aminophenyl)benzene-1,4-diamine (Bad) in a solvent and a mild acid;
(b) sonicating the reaction mixture of step (a) to obtain a homogenous dispersion followed by freezing and degassing the dispersion;
(c) heating the dispersion of step (b) to a temperature ranging from 100° C. to 200° C. for 1 to 3 days to obtain a yellowish orange colored precipitate;
(d) collecting the precipitate of step (c) by purification techniques and washing with a polar solvent to obtain a powder; and
(e) subjecting the powder collected in step (d) to solvent exchange with ethanol and drying under vacuum for 24 hours to produce a yellowish orange colored powder in 85% isolated yield.

* * * * *